US009211145B2

(12) United States Patent
Pereiro de Lamo et al.

(10) Patent No.: US 9,211,145 B2
(45) Date of Patent: Dec. 15, 2015

(54) METHOD AND SYSTEM FOR THE TREATMENT OF SPINAL DEFORMITIES

(76) Inventors: Javier Pereiro de Lamo, Madrid (ES); Juan Carlos Rodriguez Olaverri, Zaragoza (ES)

( * ) Notice: Subject to any disclaimer, the term of this patent is extended or adjusted under 35 U.S.C. 154(b) by 85 days.

(21) Appl. No.: 13/989,854

(22) PCT Filed: Nov. 21, 2011

(86) PCT No.: PCT/US2011/061573
§ 371 (c)(1),
(2), (4) Date: Aug. 13, 2013

(87) PCT Pub. No.: WO2012/074803
PCT Pub. Date: Jun. 7, 2012

(65) Prior Publication Data
US 2013/0325069 A1      Dec. 5, 2013

Related U.S. Application Data

(60) Provisional application No. 61/417,496, filed on Nov. 29, 2010.

(51) Int. Cl.
*A61B 17/70* (2006.01)
*A61B 19/00* (2006.01)
*A61B 19/02* (2006.01)

(52) U.S. Cl.
CPC ......... *A61B 17/7049* (2013.01); *A61B 17/7001* (2013.01); *A61B 17/705* (2013.01); *A61B 17/7032* (2013.01); *A61B 17/7037* (2013.01); *A61B 17/7053* (2013.01); *A61B 17/7062* (2013.01); *A61B 17/7077* (2013.01); *A61B 19/26* (2013.01); *A61B 2019/0255* (2013.01)

(58) Field of Classification Search
CPC ................. A61B 17/70749; A61B 17/7001; A61B 17/032; A61B 17/037; A61B 17/705; A61B 17/7053; A61B 17/058; A61B 17/7077

USPC .......... 600/587, 594; 606/246, 248, 266, 250
See application file for complete search history.

(56) References Cited

U.S. PATENT DOCUMENTS

| | | | | |
|---|---|---|---|---|
| 5,329,933 A * | 7/1994 | Graf | .............................. | 600/594 |
| 2006/0271050 A1 * | 11/2006 | Vallespir | .......................... | 606/61 |
| 2008/0177203 A1 * | 7/2008 | von Jako | ....................... | 600/587 |
| 2009/0012565 A1 * | 1/2009 | Sachs et al. | .................... | 606/246 |
| 2010/0063548 A1 * | 3/2010 | Wang | ............................ | 606/279 |
| 2010/0179597 A1 * | 7/2010 | Henderson et al. | ........... | 606/264 |

OTHER PUBLICATIONS

International Search Report mailed Mar. 2, 2012.

* cited by examiner

*Primary Examiner* — Kristen Matter
(74) *Attorney, Agent, or Firm* — Charney IP Law LLC; Thomas M. Fineti

(57) ABSTRACT

Devices and corresponding methods for the correction of spinal column deformities, vertebral displacements and for the surgical fixation of the spine including vertebral fixing element(s), vertebral connector element(s), and polyaxial correcting element(s) that can house along its structure varying specifically oriented correction element(s). The polyaxial correcting element(s) are mobilized with the help of correcting force element(s) that induce a three-dimensional mobilization of the polyaxial correcting elements and the vertebrae to which these are attached. Longitudinal spinal fixing element(s) provide for the definitive fixation of the spine. The longitudinal spinal fixing element(s) are joined and fixed to the vertebral fixing element(s) or to permanent vertebral connector element(s). The three-dimensional aspect of the spine is accurately envisioned prior to surgery allowing a caregiver to both create a treatment plan and make intra-operative changes as needed in relation to the correction of the spine.

16 Claims, 25 Drawing Sheets

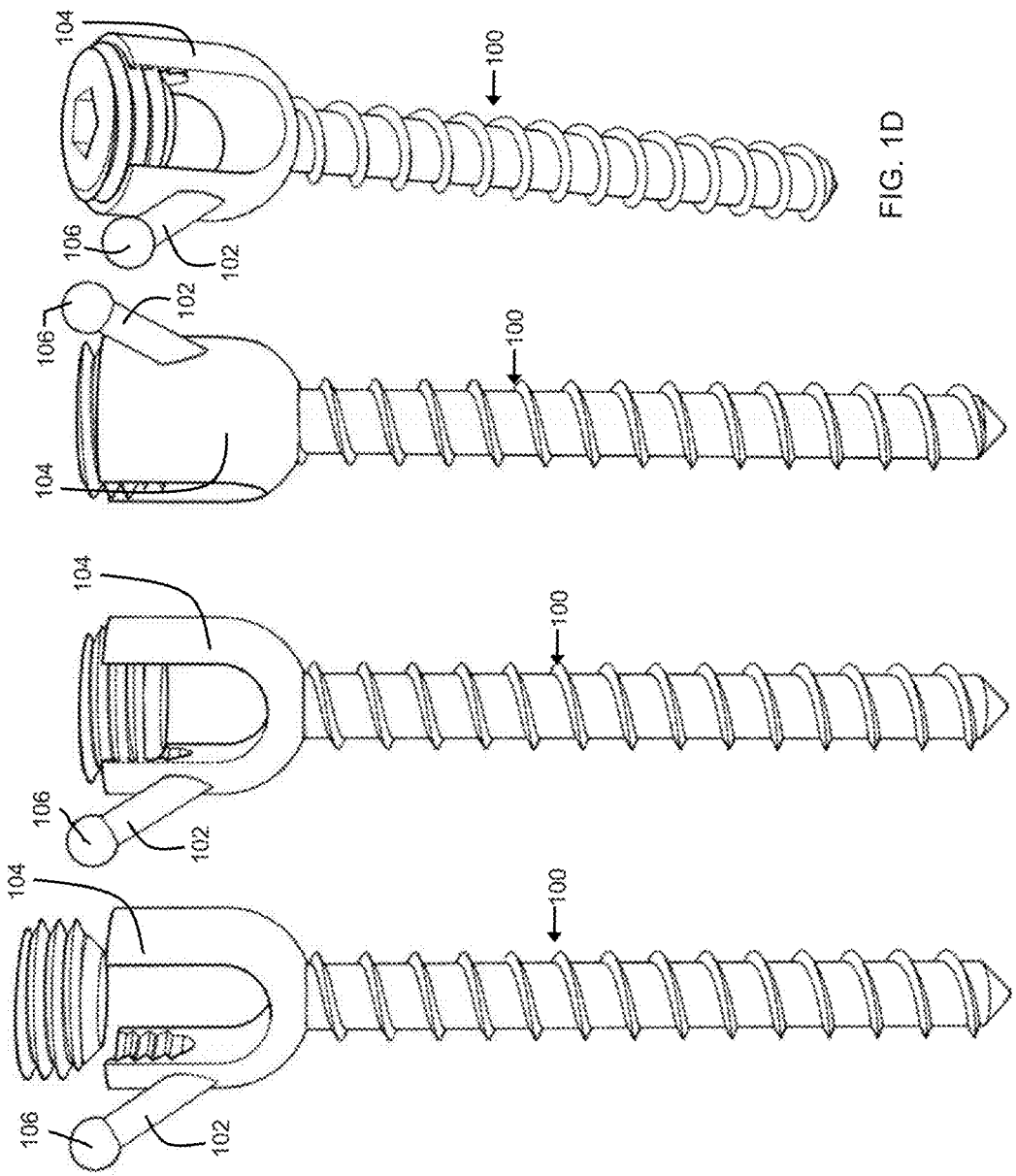

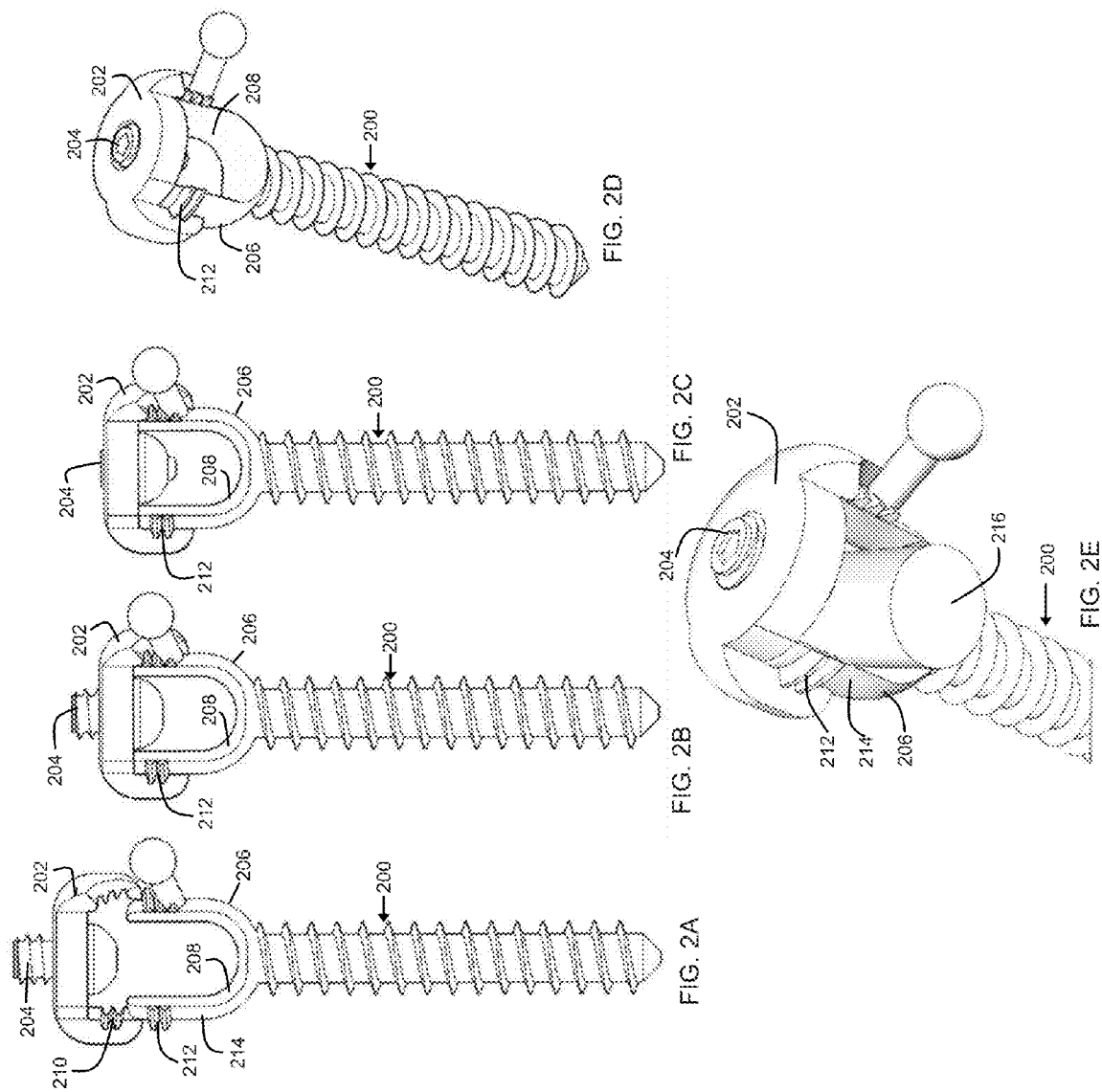

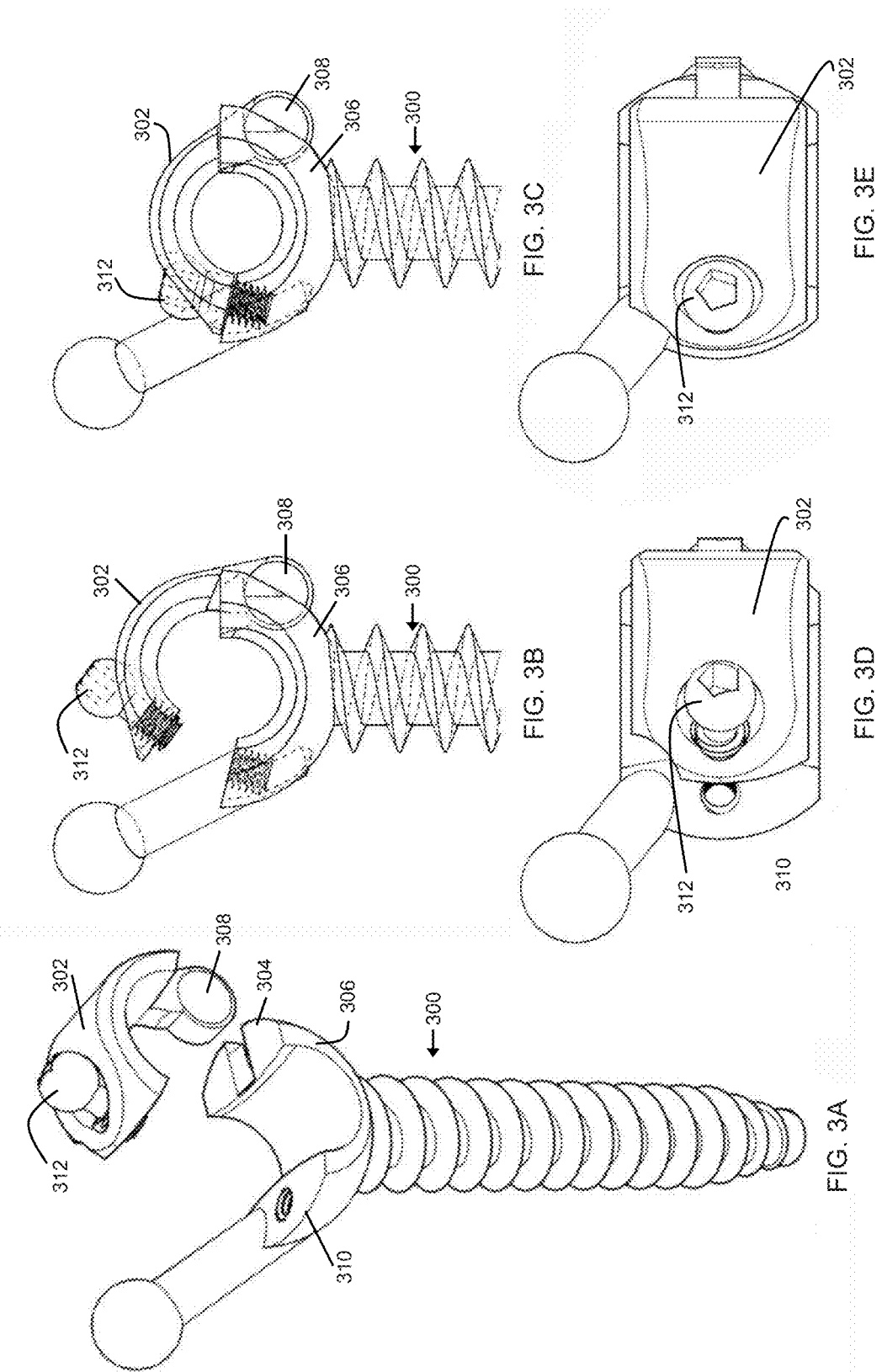

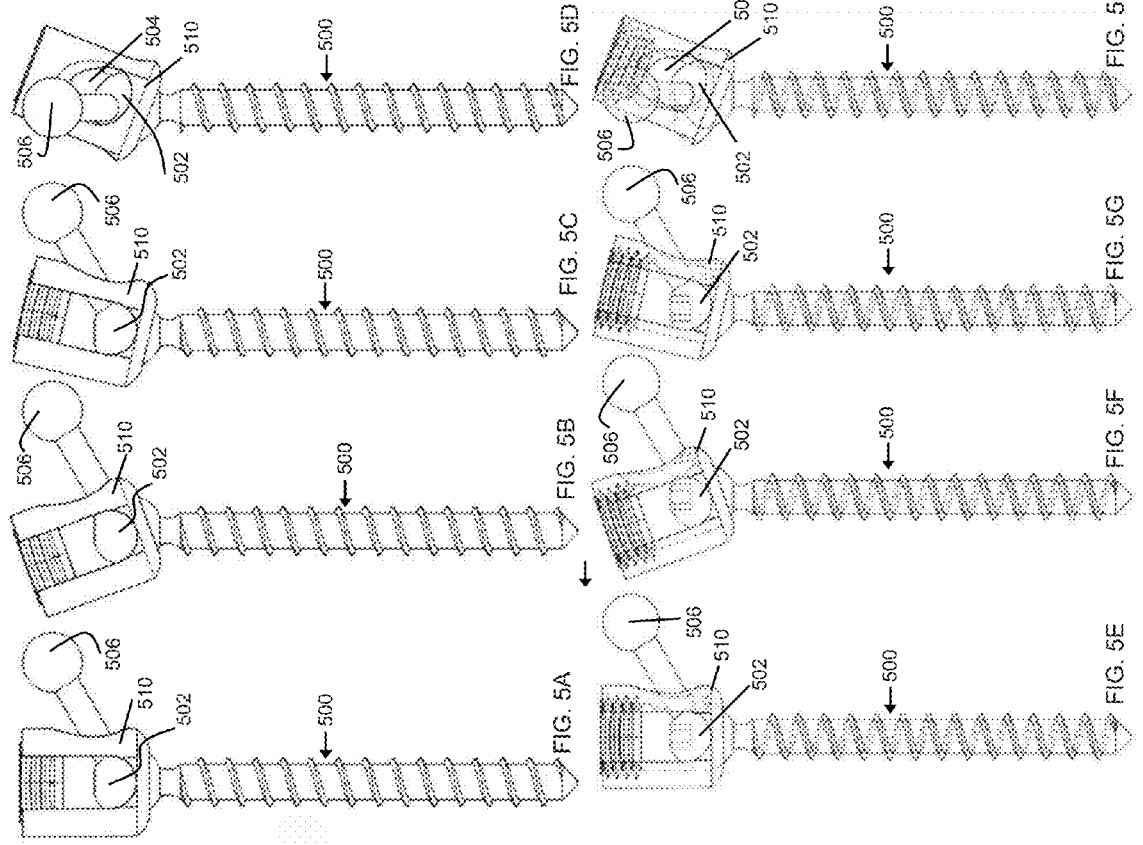

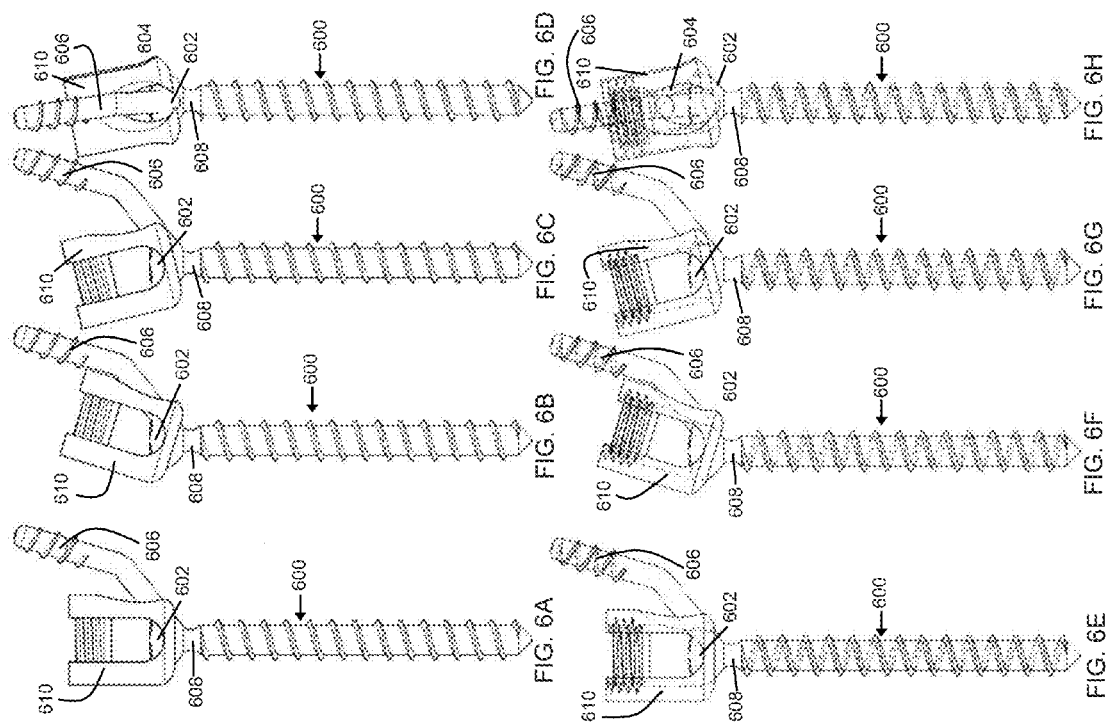

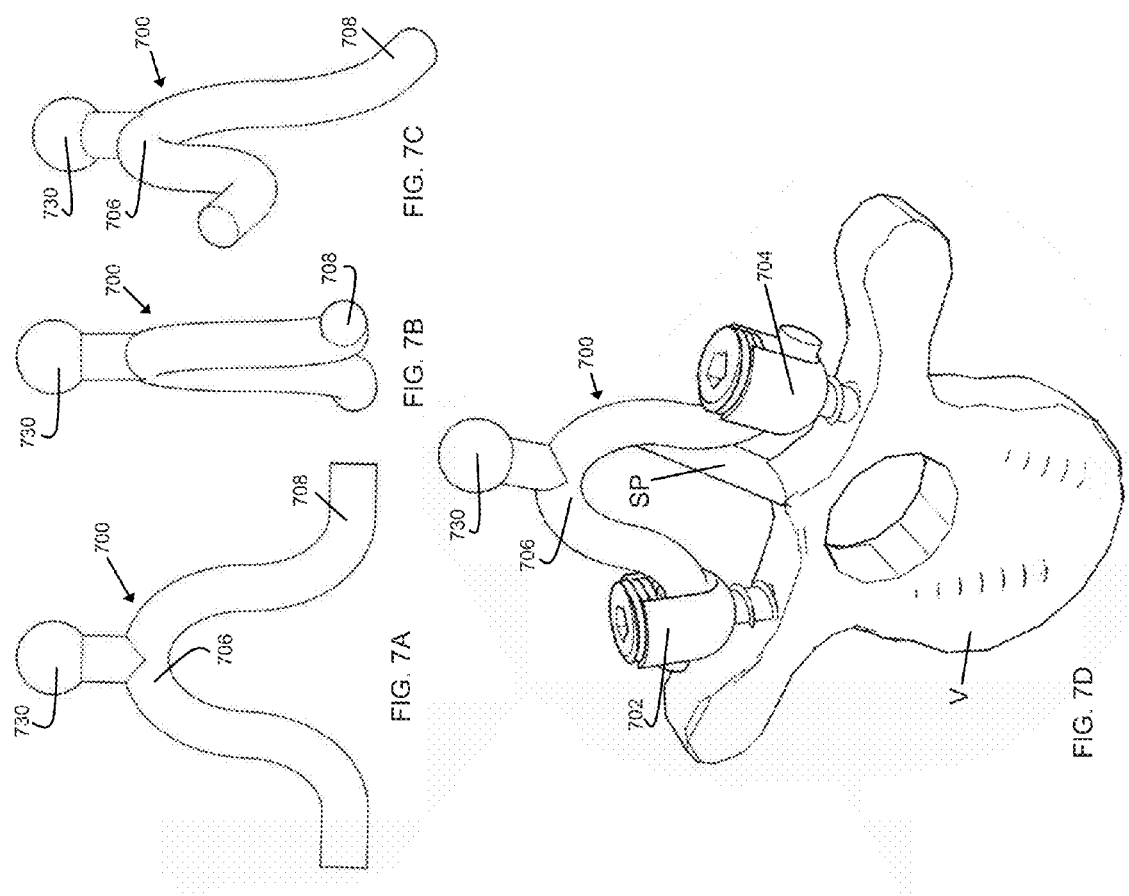

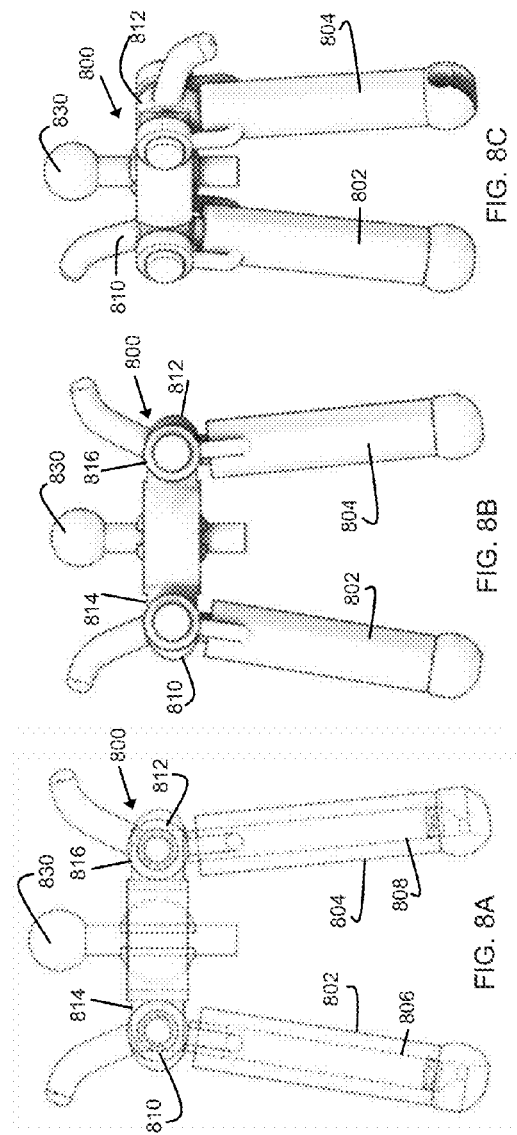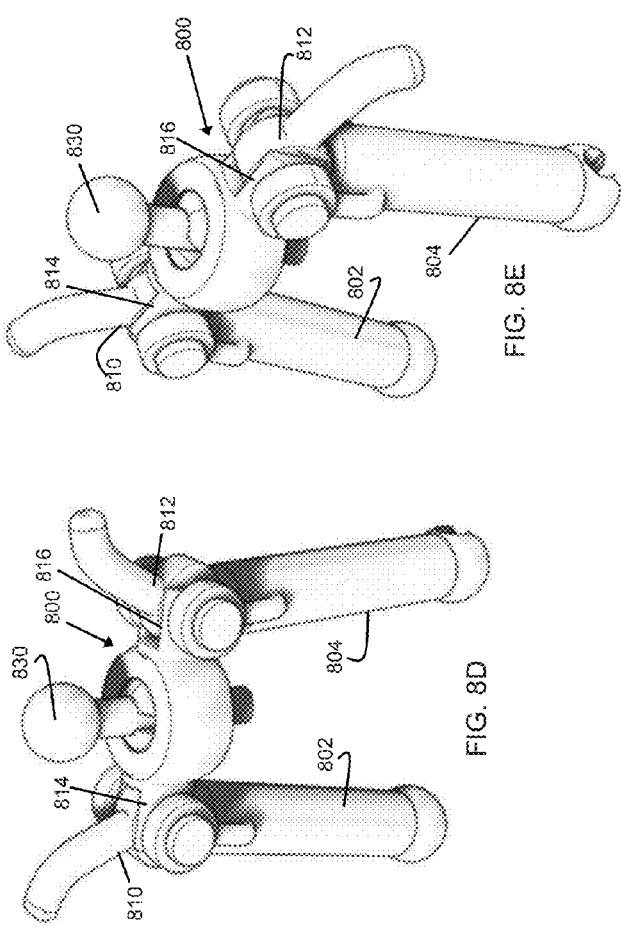

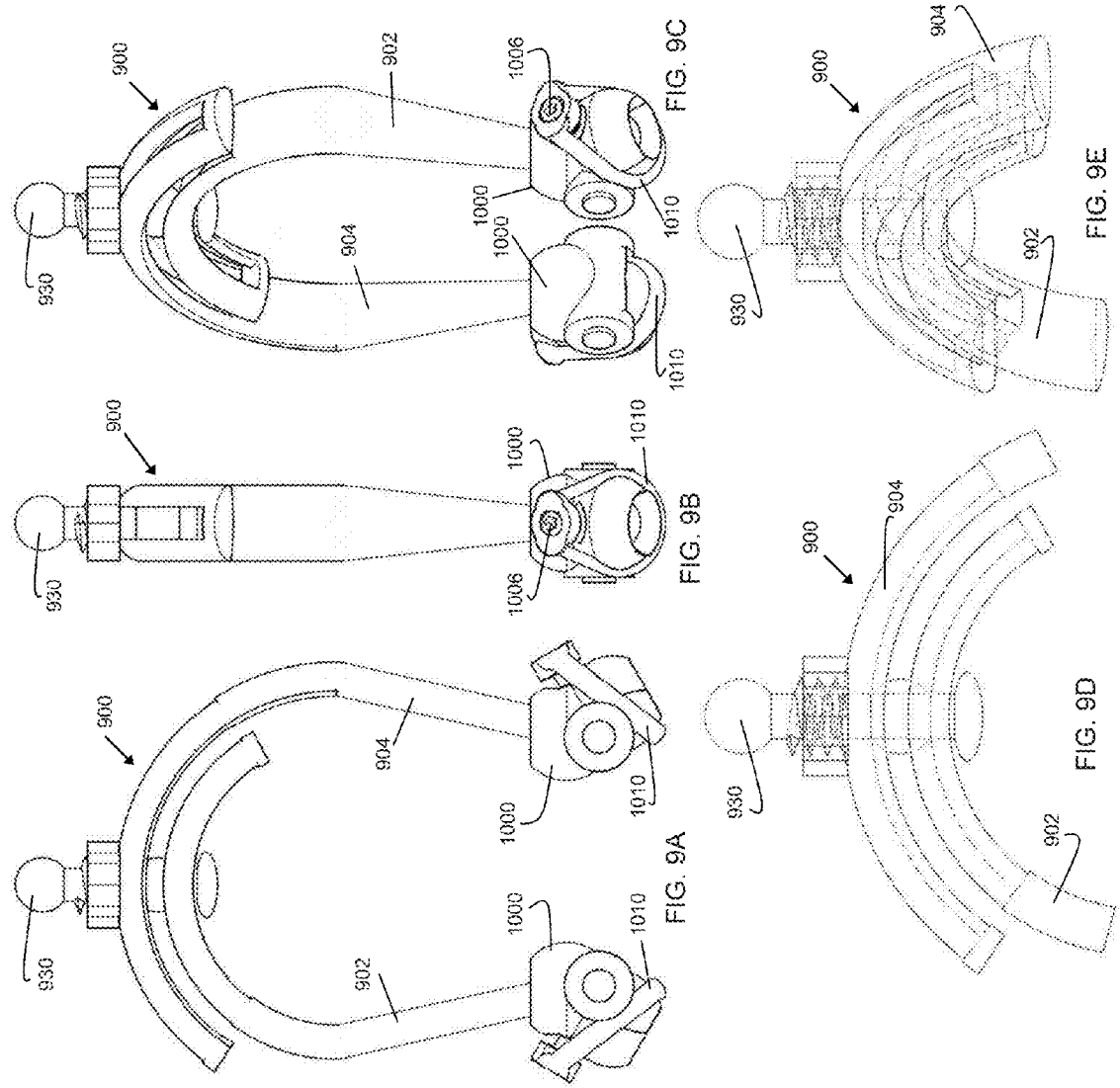

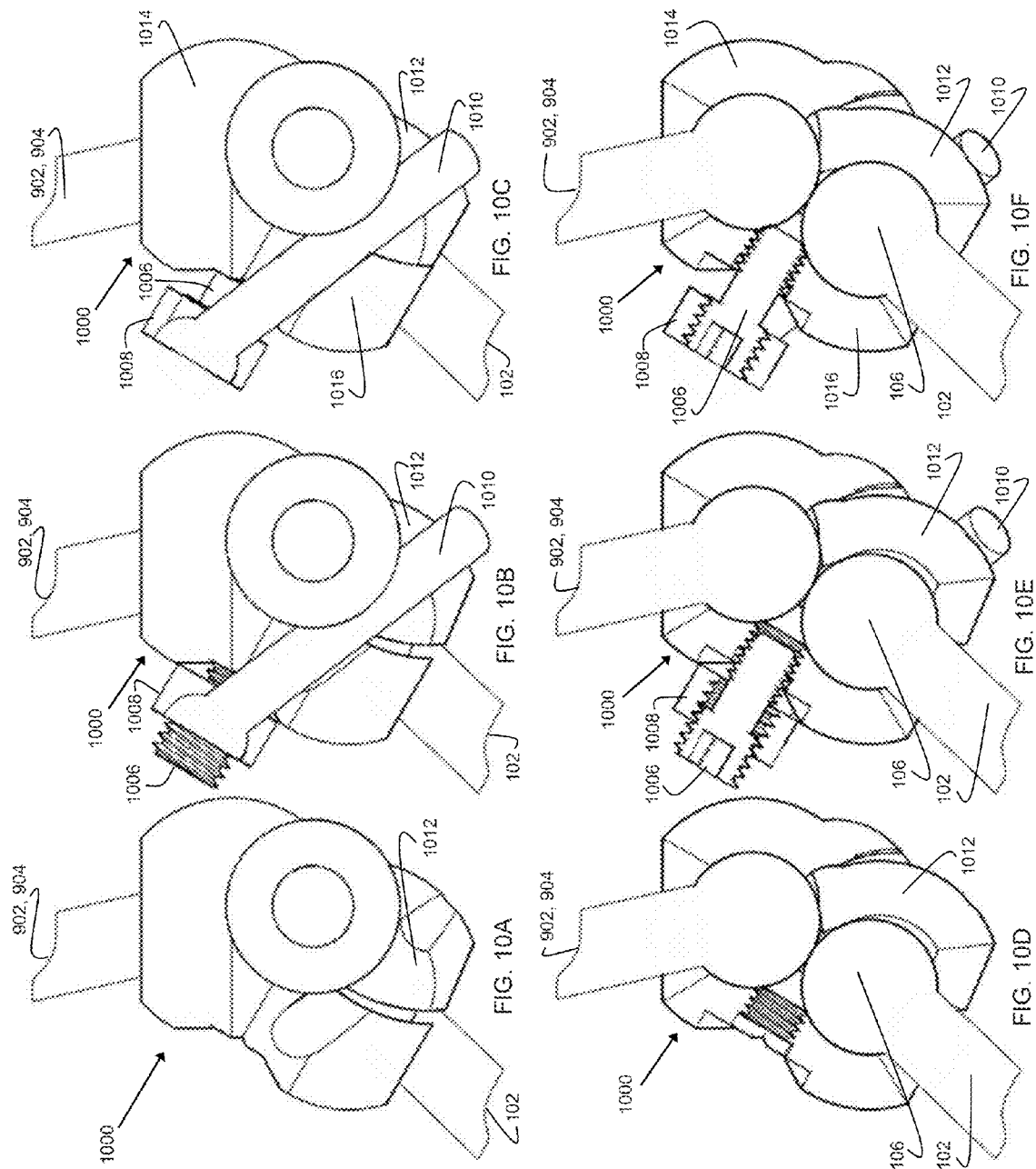

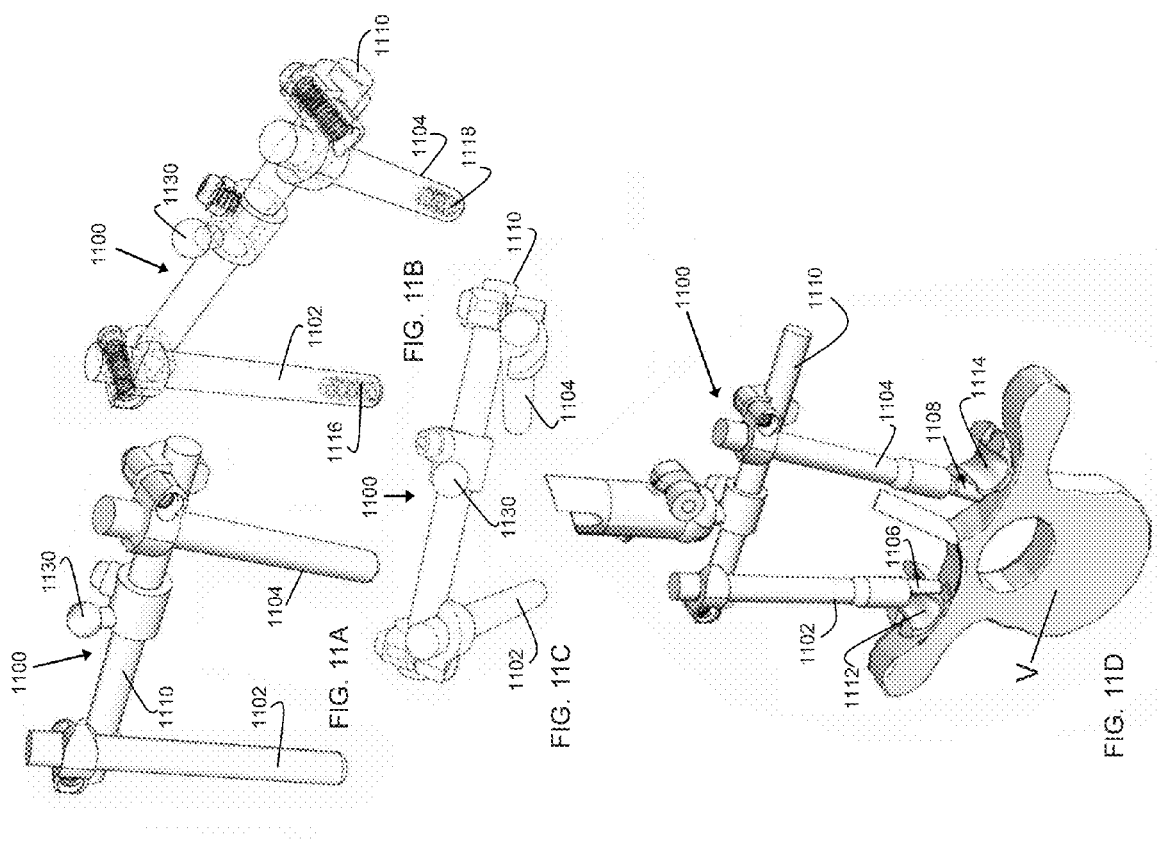

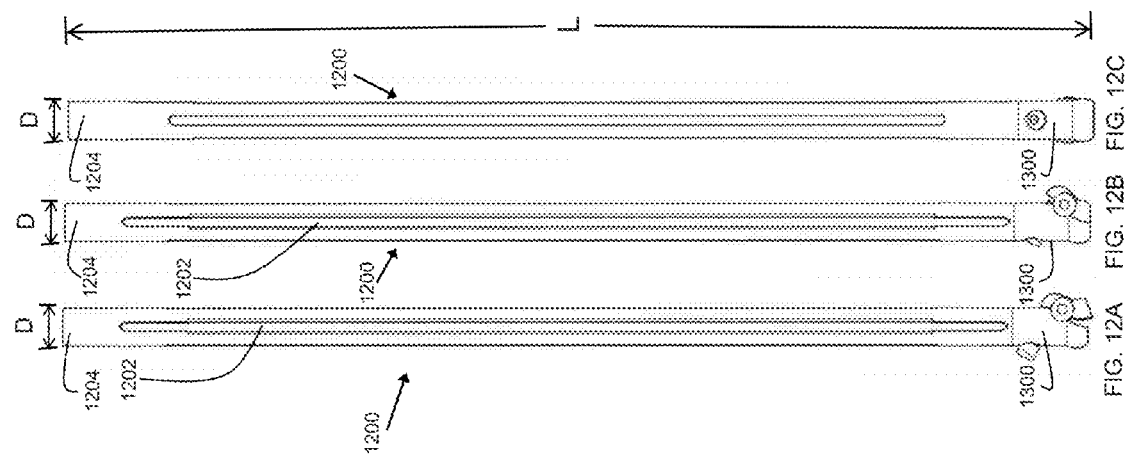

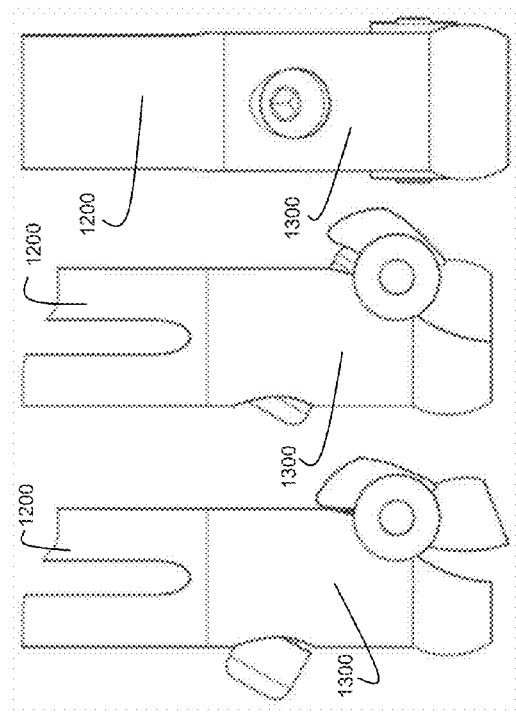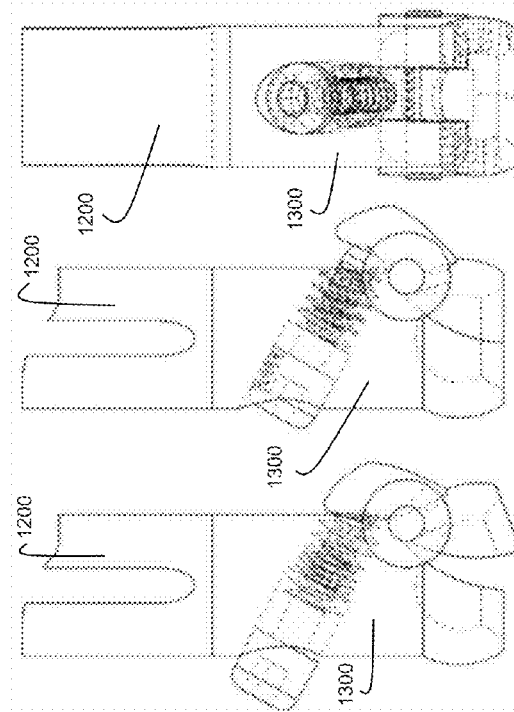

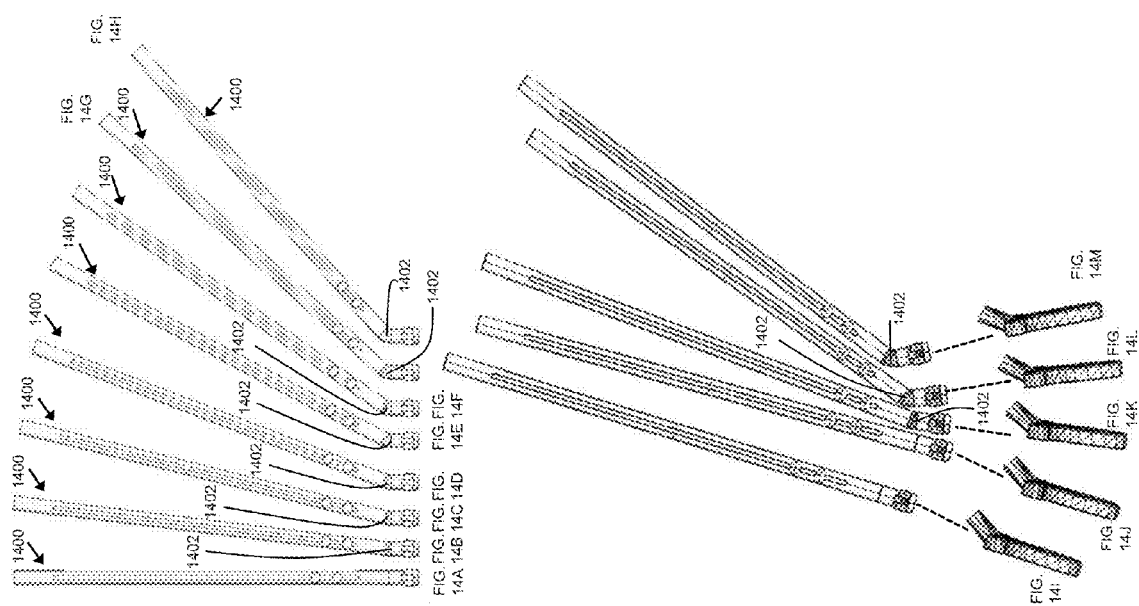

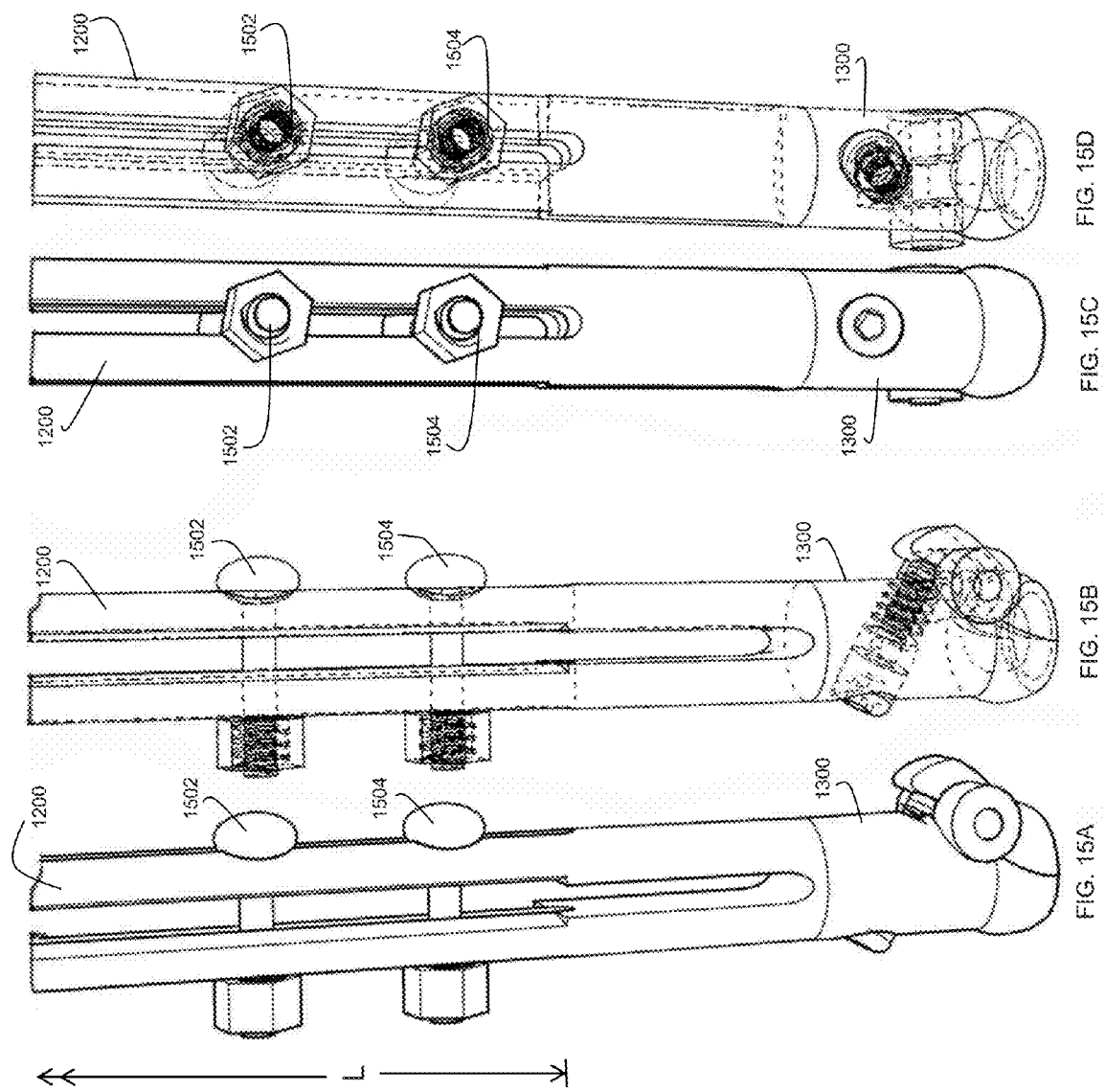

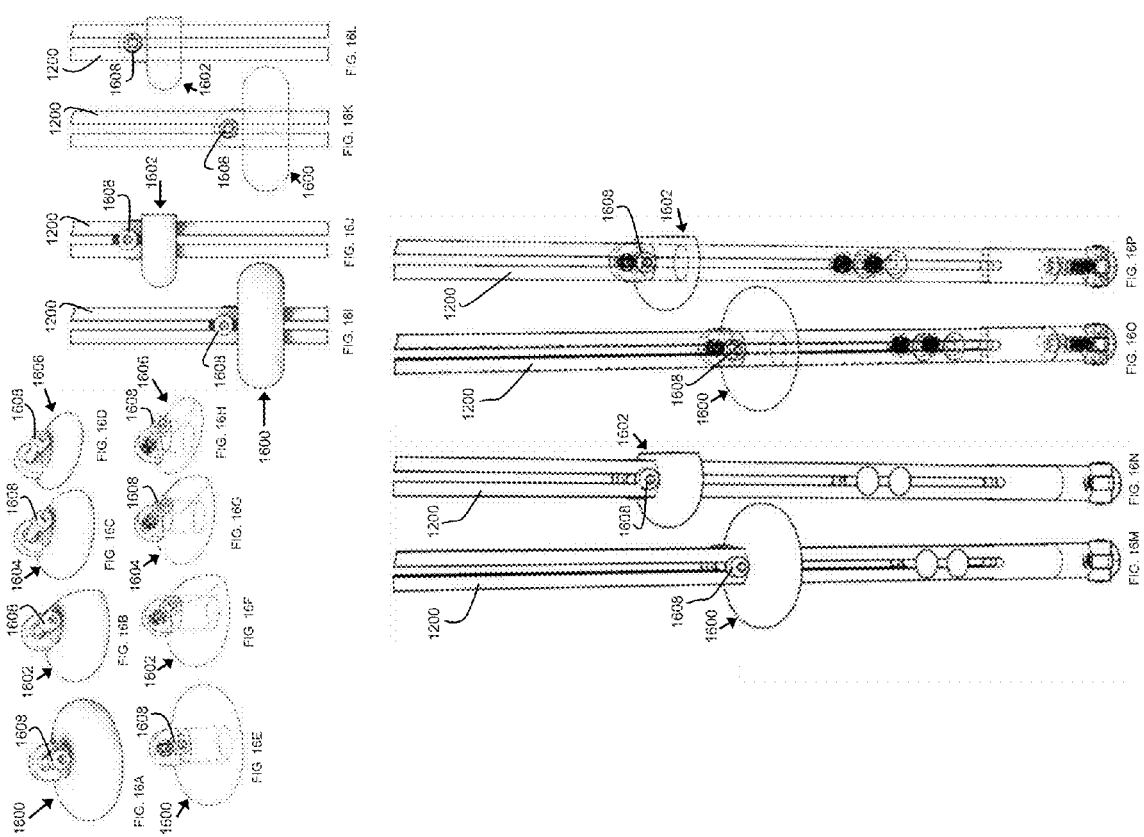

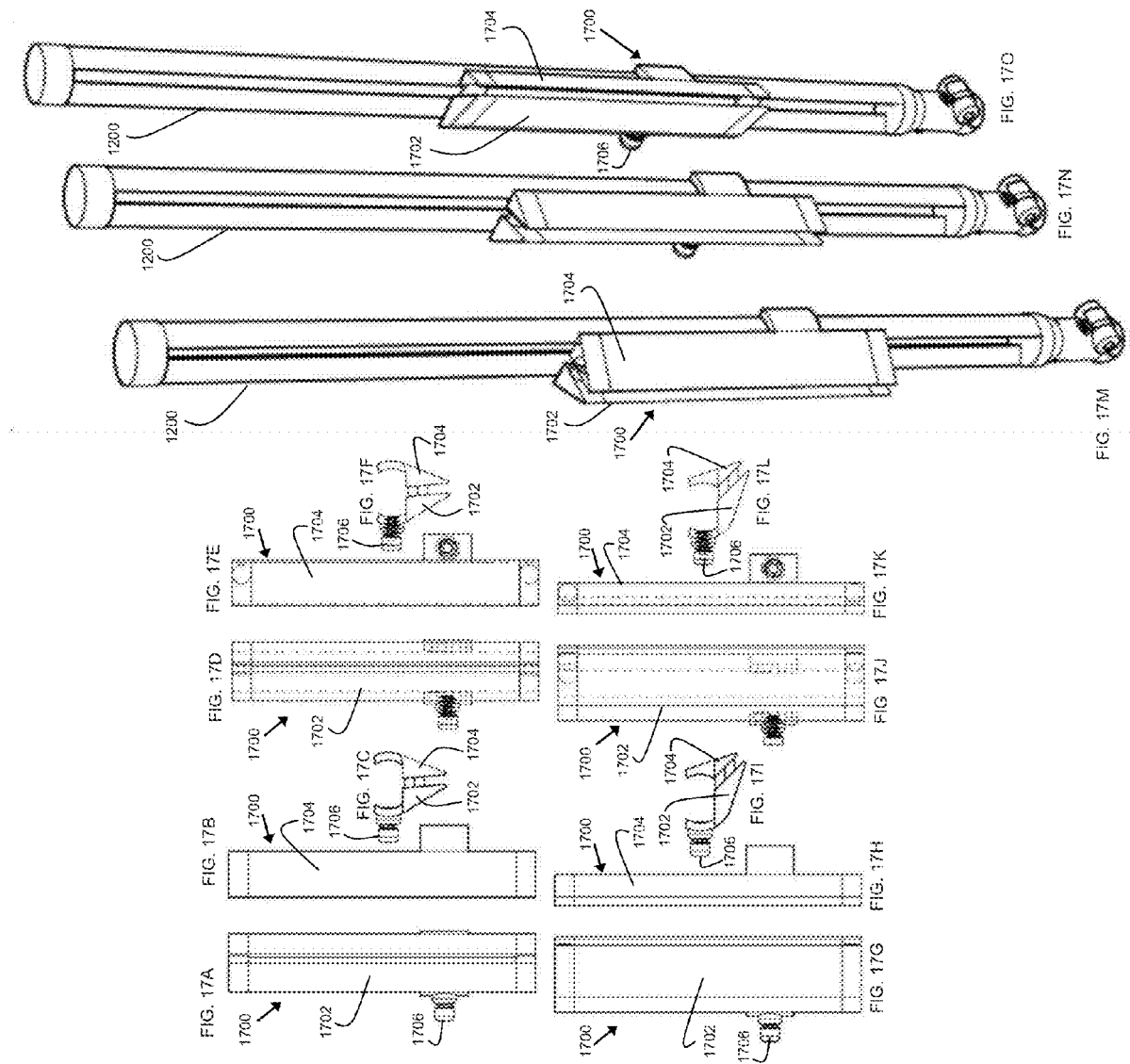

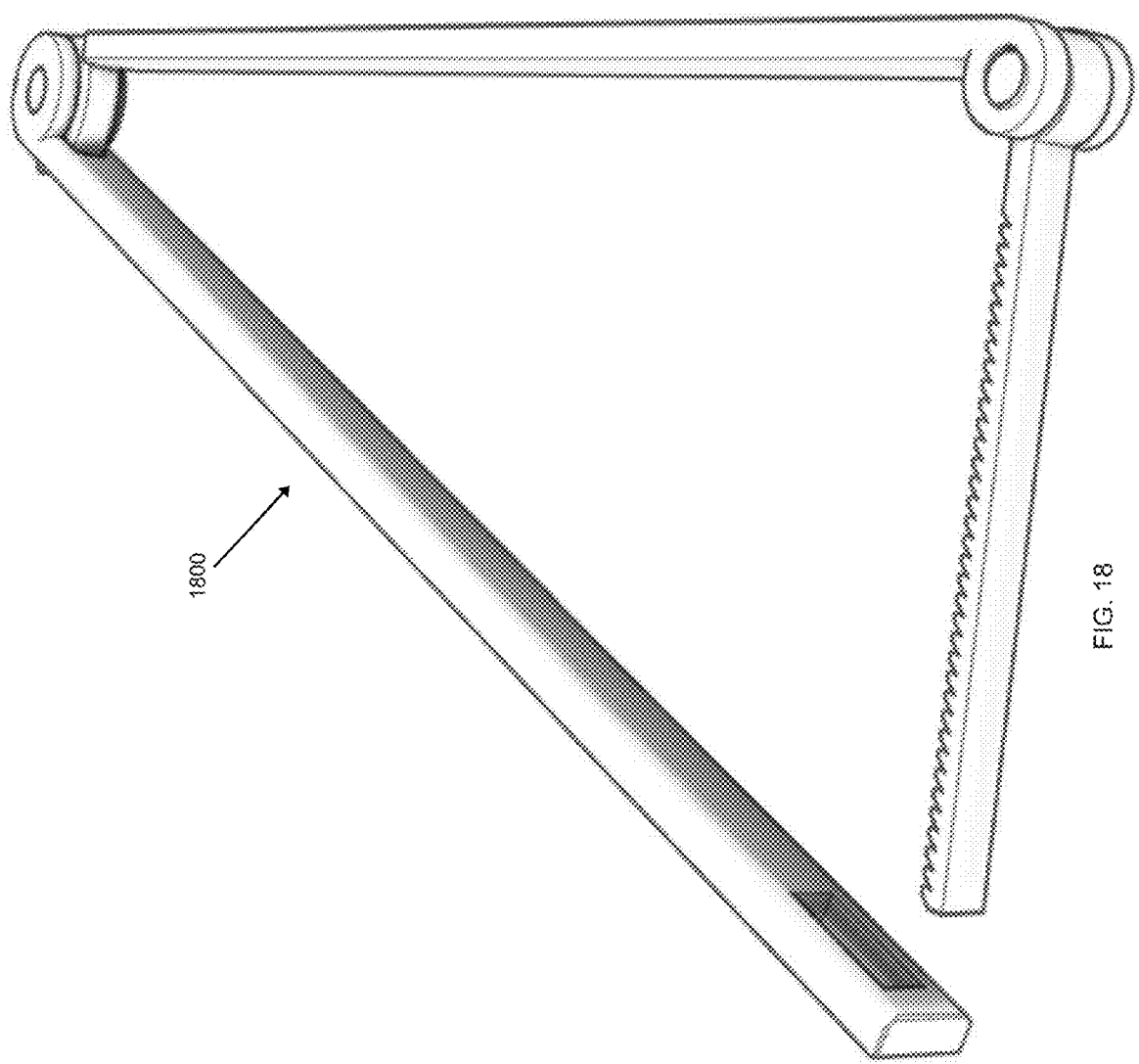

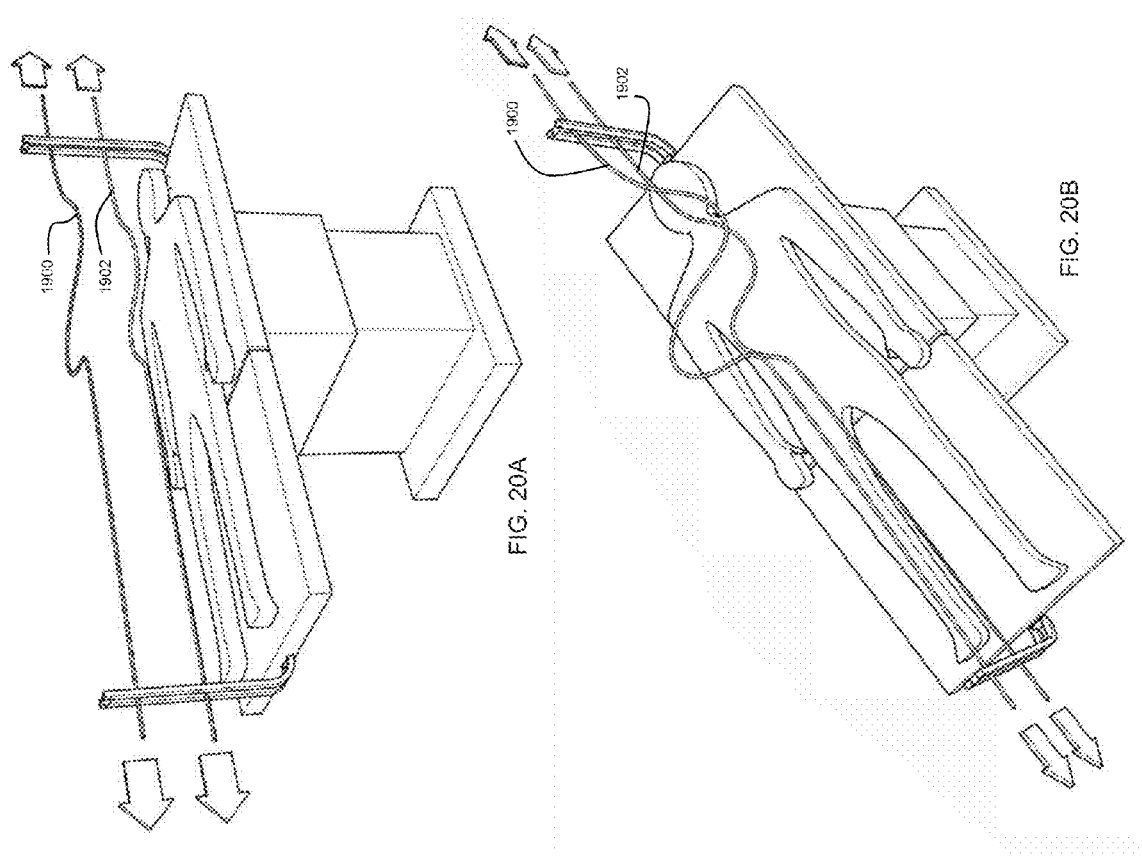

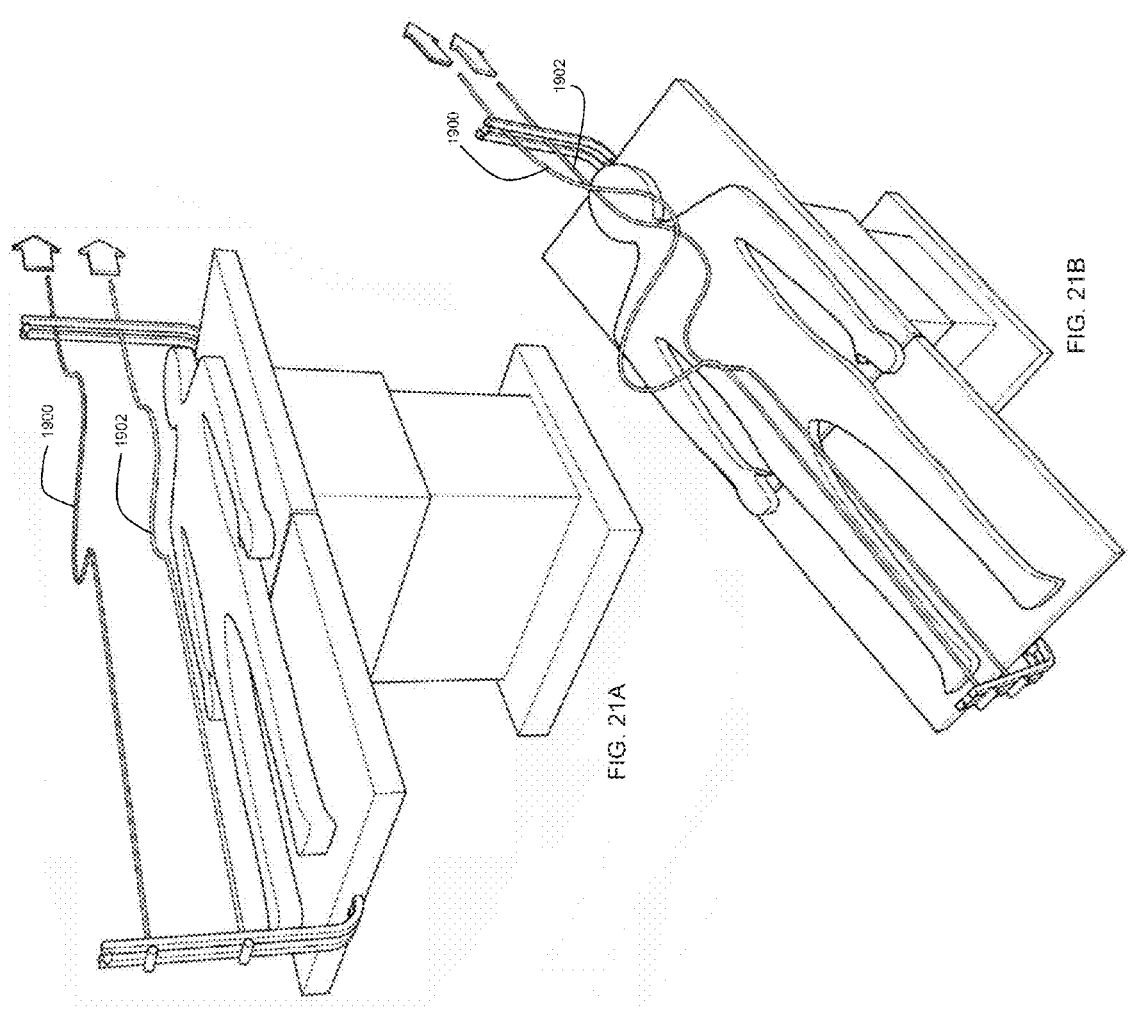

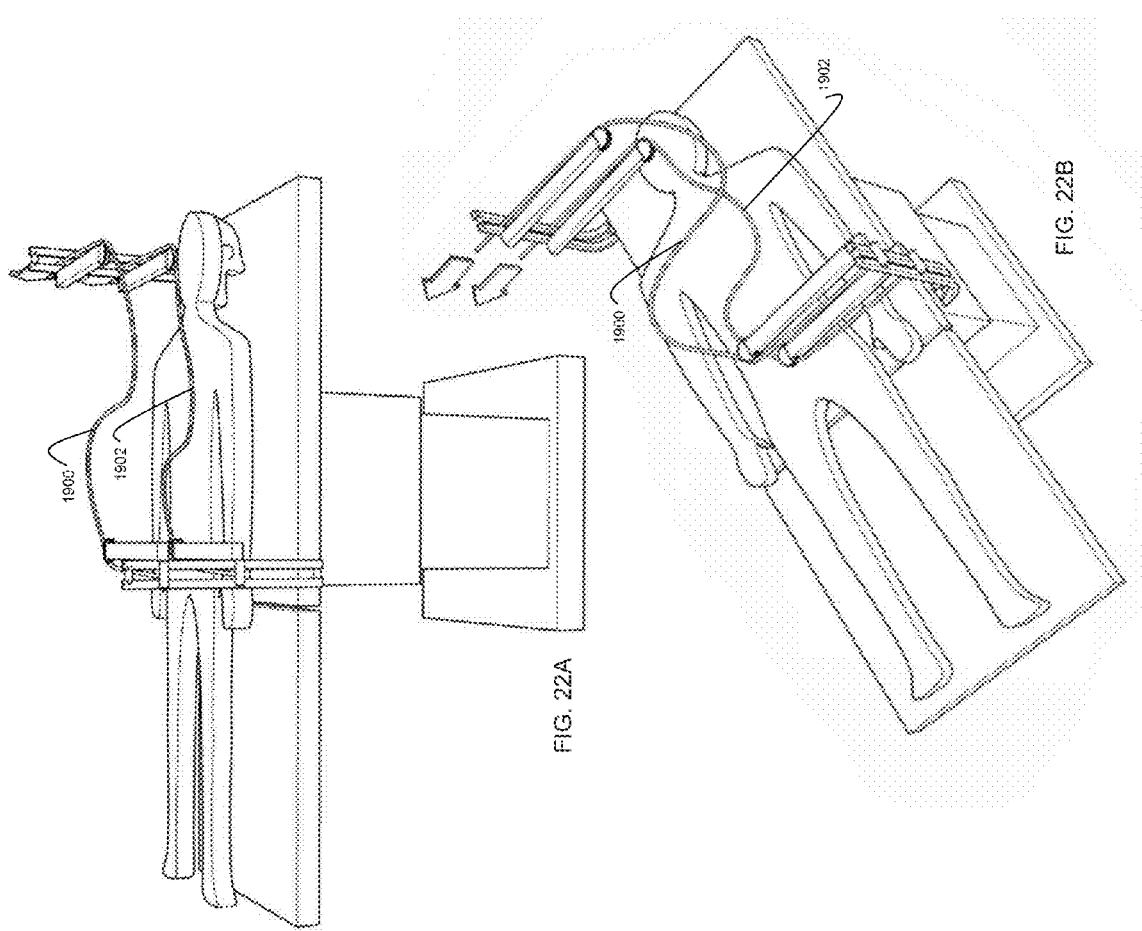

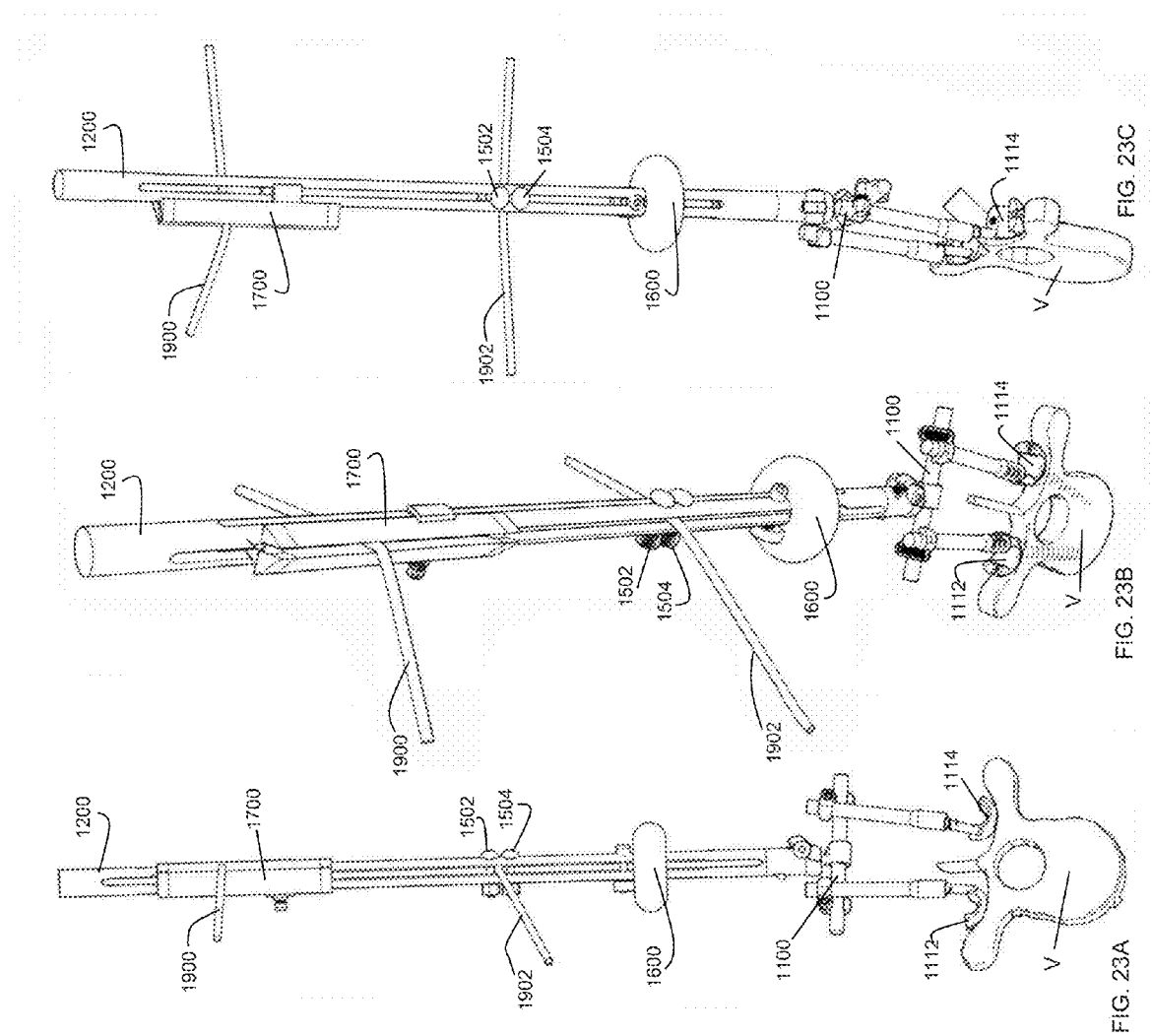

METHOD AND SYSTEM FOR THE TREATMENT OF SPINAL DEFORMITIES

CROSS-REFERENCE TO RELATED APPLICATIONS

This application claims priority to the U.S. provisional application 61/417,496 filed on Nov. 29, 2010 and PCT International Application PCT/US2011/061573 filed on Nov. 21, 2011, the contents of which are incorporated in its entirety.

FIELD OF THE INVENTION

The present invention relates to the methods and apparatuses employed for the correction of physical deformities of the spine and the methods and apparatuses utilized for the fixation of the spine and its vertebral members. More particularly, this invention specifically aims to correct accurately a misaligned/malaligned spine in a pre-determined and planned way, and to maintain the correction obtained by means of one or more longitudinal spinal fixing elements that are securely fixed to the vertebral members being corrected.

BACKGROUND OF THE INVENTION

The Normal and Deformed Spine

The osseous spine is composed of individual vertebral members or vertebrae, which are distributed along the length of the vertebral column. These vertebrae have an anterior wider portion known as the body of the vertebra, and a posterior osseous are with prominences (spinous process, transverse processes, pars interarticularis, superior and inferior facets), where the muscles of the back and ligamentous structures insert.

The normal human spine has seven vertebrae in the cervical region, twelve vertebrae in the thoracic region, five vertebrae in the lumbar region, five vertebrae that are fused together forming the sacrum and two or three small distal and inferior vertebrae that constitute the coccyx. The cervical, thoracic and lumbar segments of the normal human spine adopt an "S" shape form as viewed from the lateral aspect, (sagittal or lateral view), and a straight aspect as viewed from the front or the back (frontal or coronal view).

Each vertebrae of the spine has a particular shape and size, depending on its localization, so that the cervical vertebrae are smaller and have more degrees of movement in all planes, thoracic vertebrae are more rigid and stable because they are connected to the rib cage and the lumbar vertebrae situated closer to the pelvis and sacrum are bigger, heavier and stronger as they have to bear greater stresses and loads.

Every vertebral member of the spine has a particular orientation in space, such that the normal human spine has no lateral tilt when viewed from the front, and a specific upwards or downwards inclination with respect to the horizontal plane when viewed from the lateral. The size, shape and orientation of all the vertebrae of the spine determines its sagittal and coronal contour.

The spine can be functionally structured in vertebral units. A vertebral unit is comprised of two adjacent vertebrae, the interposed intervertebral disc, the facet joints between the two adjacent vertebrae and the ligaments, muscles and fascial insertions between the vertebrae.

As viewed in the sagittal plane, an anterior convex profile of a segment of the spine is termed lordosis and an anterior concave profile of a segment of the spine is known as kyphosis. The normal human spine has a cervical segment showing an anterior convexity (cervical lordosis), an anterior concave thoracic segment (thoracic kyphosis), and a lumbar region with anterior convexity (lumbar lordosis). In a normal balanced spine, the head of the subject and the axis of the vertebral column are centered over the sacrum in both the frontal and the sagittal planes.

The spine of individual people can be deformed by a wide variety of causes such as idiopathic, congenital, traumatic, infectious, degenerative and malignant processes. The curvature of the normal straight aspect of the spine as viewed in the coronal view is commonly known as scoliosis. An unbalanced sagittal profile of the curvature of the spine when increasing the normal direction of the convexity or concavity of a segment of the spine is commonly referred with the prefix "hyper" whereas a decrease of the normal curvature is referred with the prefix "hypo", being therefore possible to have a hyperlordosis of the cervical and lumbar spine regions and a hyperkyphosis of the thoracic spinal segment. In an opposite way it is also possible to have a hypolordotic cervical and lumbar segment of the spine when its normal curvature is decreased and a hypokyphosis of the thoracic segment. In cases where the normal curvature of a segment of the spine as viewed in the sagittal plane is not only decreased but reversed there can be an abnormal kyphosis of the cervical and lumbar regions or an abnormal lordotic thoracic spine.

In some cases one or more vertebrae can be displaced over the inferior vertebra following a plane that runs almost parallel to the vertebral plate of the inferior vertebral body; that is, olisthesis. If this displacement is observed in the sagittal plane there can be an anterolisthesis when the superior vertebra displaces anteriorly over the vertebra located immediately below; or retrolisthesis, when the displacement of the superior vertebra is posterior over the vertebra situated below. In other cases the olisthesis phenomenon can be observed on the frontal plane of the spine, resulting in laterolisthesis.

In many cases the loss of the normal aspect and balance of the spine is concomitant with the deterioration of its mechanical integrity which may lead to a diminished pulmonary function, pain and in severe cases to the inability to maintain the functional integrity of the neural elements contained within the spine such as the spine cord and the spinal nerves. In such circumstances it may be necessary or desirable to correct and fix the spine with the intention to regain a satisfactory mechanical stability, to improve pain and to prevent the abnormally balanced spine from causing future or further damage to the neural elements that it contains.

For the correction and fixation of a deformed spine, physical, orthopedic or surgical methods can be employed. The surgical interventions necessary to correct a spine deformity require the exposure of the vertebral elements of the spine to be corrected and this can be done with a surgical approach from the posterior aspect of the subject. After the exposure of the vertebral elements of the spine has been completed it may be necessary to perform an "in situ" fixation of the vertebral elements. If correction of a deformity is required, the spine and the vertebral elements can be manipulated and mobilized before their definitive fixation.

Most common surgical systems employed for the fixation and the correction of spine lesions and deformities include the use of two longitudinal spinal fixing elements running along the sides of the vertebral elements, usually a metal alloy rod or plate. These longitudinal spinal fixing elements fix and maintain the vertebrae together by means of vertebral fixing vertebral elements. These vertebral fixing elements can be of different types such as pedicle screws, laminar, pedicle or transverse process hooks and laminar wires or cables.

All the deformities of the spinal column, even the most subtle deformities are a three-dimensional deformity problem, as the displacement of the vertebral elements over one axis of the space is almost invariably accompanied by the displacement of the same vertebral elements in the other two axis of the space. In more marked spinal deformities such as those occurring in severe scoliotic patients, the lateral deviation of the spine, as visualized in the coronal plane, is associated with a change in the sagittal profile of the spine and a change in the length of the spine that increases with the severity of the deformity. In these complex spine deformities, as the spine is deformed and the vertebral elements are displaced in the X, Y and Z axes of the space, the vertebral elements themselves also suffer a change in their spatial orientation, and even are deformed in their anatomy with loss of their normal mid-sagittal symmetry. In this way we find that in a subject suffering scoliosis, the anterior aspect of the vertebral elements that deviate laterally from the midline of the body, as viewed from the front, suffer a rotation in the horizontal or axial plane (rotation through the Z axis) of the most anterior part of the vertebrae in the same direction as the frontal deviation. At the same time the vertebral elements suffer a change in their inclination as viewed from the lateral side (rotation through the Y axis), and also a change in their inclination or tilt as viewed from the front (rotation through the X axis).

So, what it is commonly referred as scoliosis or frontal plane deviation of the vertebral column is the end result of a much more complex deformity process that involves a true translational and rotational phenomenon of the vertebrae and the whole spine with severe anatomic deformities of the vertebral elements.

Surgical Correction and Fixation Systems of the Spine

The earlier correction and fixation systems developed in the 20$^{th}$ century and employed for the surgical treatment of spine deformities, applied distraction forces to the exposed spine on the concavity of the deformity to straighten the spine and thus improve its coronal aspect.

The Harrington distraction rod was developed with this distraction concept by Paul Harrington. The later applied a second rod working in compression on the convexity of the curve to improve spinal fixation and the stability of the final construct. The Harrington rods were attached to the vertebrae by means of hooks fixed onto the posterior osseous aspects of the vertebrae. Two of these hook type vertebral fixing elements could be disposed into compression by holding onto the same or adjacent vertebrae in opposite directions acting in this way as a stronger fixing element of the spine. The disposition of different fixation elements along the spine and the use of the rods in compression or distraction mode along their length improved the corrections of the spine achieved and the strength of the fixation. However, the use of distraction and compression forces in these earlier spine instrumentations led in many cases to an abnormal straightening of the physiological "S" shape sagittal balance of the spine, which was in itself a cause of discomfort, pain and functional impairment.

Improvements of spinal fixation instrumentations by Pedro Luque introduced the concept of segmental fixation of the vertebral elements using multiple wires and cables that were fixed to the rods along the entire length of the spine being corrected, resulting in a medial translation and approximation of the displaced vertebrae to the longitudinal rod spinal fixing element that could be previously contoured in the sagittal plane in a more satisfactory aspect than the Harrington rods.

Later designs of spine instrumentation, such as the Cotrel-Dubousset system, rotated the spine transforming its frontal curve deviation into a sagittal curve by rotating a contoured longitudinal rod spinal fixing element secured to the vertebral fixing elements inserted on one side of the vertebral column. However, these segmental derotation systems focused on good coronal and sagittal alignment of the spine, the axial rotation of the individual vertebrae was for its major part not considered or it was taken as a collateral pay-off of the correction maneuvers which led in many circumstances to an increased axial malalignment of the vertebrae being corrected.

More recent developments of surgical correction instrumentations claimed the ability to derotate the displaced vertebrae into a more satisfactory axial orientation by direct manipulation and derotation of an individual vertebra or a few vertebrae solidarily. This axial derotation of the vertebrae is done after the correction of the coronal deviation of the spine is performed and in other cases at the same time of the correction of the coronal deformity as is the case with the Coplanar systems. One example of such surgical correction is Direct Vertebral Rotation, With the introduction of pedicle screw type vertebral fixation elements for the correction of the spine deformities, a bigger correction power was provided to the surgical instrumentations to align and rotate the spine and at the same time a stronger fixation of the longitudinal rods to the vertebrae was obtained.

Present surgical spine fixation systems make use of two longitudinal spinal fixing elements (commonly rods) for the definitive fixation of the spine, placing them on each side of the vertebral column, as it has been observed that fixation of the spine with only one longitudinal spinal fixing element leads to material fatigue and failure with worse clinical results.

Problems Inherent to Current Spine Deformity Correction and Fixation Systems

In current surgical spine instrumentations, correction of the spine is done through the sequential and individualized mobilization of the displaced vertebrae or the combined mobilization of a few or all of the vertebrae by means of the vertebral fixing elements attached to one side of the vertebrae. These surgical spine instrumentations have the disadvantage of distributing the forces employed for the correction of the spine through only half of the vertebral fixation elements that will be finally included in the definitive spine fixation construct.

Most present spine deformity correction and fixation systems make use of the longitudinal spinal fixing elements for the mobilization and correction of the vertebrae after these are secured or fixed to the vertebral fixing elements attached to the vertebrae. This use of the longitudinal spinal fixing elements for the correction of the spine deformity, while not difficult in cases of small deformities, can become challenging even for the most experienced surgeon when the spine is severely deformed. In cases such as this, the introduction of the longitudinal spinal fixing element in the vertebral fixing elements becomes more difficult and the correction of the spine with the longitudinal spinal fixing element in place is cumbersome, the result being that a significant part of the final correction obtained is dependent on the experience of the surgeon.

The distribution of the correcting forces through only one side of the vertebrae and the vertebral fixing elements on this side of the spine increases the loads and stresses over these vertebral fixing elements and the corresponding osseous elements of the vertebrae increasing the chances for loosening or breaking of the vertebral fixing elements and the vertebrae with the possibility of causing neural damage.

As a direct consequence of doing the correction maneuver of the deformed spine over the vertebral fixing elements on one side of the spine and the fixation of the spine being corrected on one side first, usually the side from where the correction is done, the end result is a definitive spinal fixation construct with two longitudinal spinal fixing elements that bear different stresses and loads. While most of the forces are supported by the longitudinal spinal fixing element that is placed and fixed first, the longitudinal spinal fixing element on the other side of the vertebral column will only partially share the loads and stresses to which the corrected spine is subject to, therefore increasing the chances for material fatigue and failure of the definitive spinal fixation construct and for loosening of the spinal correction achieved during surgery.

Current Needs of Spinal Correction and Fixation Systems

There is therefore a need in the field of spinal surgery for a method of vertebral correction and a fixation system that can do an accurate and precise correction of an unbalanced spine.

There is further a need in the field of spine surgery for a true three-dimensional correction method that mobilizes the vertebrae in the three-dimensional space as desired.

There is a more specific need for a spine surgical correction method and fixation system that can do an accurate three-dimensional correction of the spine as determined and planned before surgery.

The need exists also for a versatile three-dimension spine correction method and fixation system that will allow for an easy intra-operative modification of the pre-surgically planned correction that will result in an as expected correction of the spine deformity.

A need also exists for a method for the surgical correction of spine deformities that will not be intensively dependent on the initial positioning of the vertebral fixing elements and the extensive experience of the surgeon but rather rest upon the reliability and accuracy of the correction method and the instrumentation.

These and other objects are achieved in the present invention. There has thus been outlined, rather broadly, exemplary features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that equivalent constructions insofar as they do not depart from the spirit and scope of the present invention, are included in the present invention.

For a better understanding of the invention, its operating advantages and the specific objects attained by its uses, reference should be had to the accompanying drawings and descriptive matter which illustrate preferred embodiments of the invention.

BRIEF DESCRIPTION OF THE FIGURES

FIGS. 1A through 1D depict multiple views of an embodiment of monoaxial pedicle screw(s), FIG. 1A being a partially exploded view.

FIGS. 2A through 2E illustrate multiple views of an embodiment of a monoaxial pedicle screw with a cap screw in the shape of an inverted hat, FIG. 2E being a partial enlarged view.

FIGS. 3A through 3E illustrate multiple views of an embodiment of a monoaxial pedicle screw with a hinge type closing cap screw, FIG. 3A being a partially exploded perspective view and FIGS. 3B and 3C being partially transparent views.

FIGS. 5A through 5H illustrate multiple views of an embodiment of a polyaxial pedicle screw, FIGS. 5E through 5H being partially transparent.

FIGS. 6A through 6H illustrate multiple views of another embodiment of a polyaxial pedicle screw, FIGS. 6E through 6H being partially transparent.

FIGS. 7A through 7C illustrate multiple views of an embodiment of a permanent vertebral connector element in the form of a bent rod and FIG. 7D further illustrates a perspective view of the manner in which the vertebral connector is used to connect two pedicle screw vertebral fixing elements inserted in the same vertebra.

FIGS. 8A through 8E illustrate multiple views of an embodiment of a compass type temporary vertebral connector, FIG. 8A being partially transparent.

FIGS. 9A through 9E illustrate multiple views of an embodiment of an arch type vertebral connector element, FIGS. 9D and 9E being partially transparent view of the proximal end part of this arch type vertebral connector element.

FIGS. 10A through 10F further illustrate multiple views of the double polyaxial joint of the arch type vertebral connector element of FIGS. 9A through 9E, FIGS. 10D through 10F being cross-sections.

FIGS. 11A through 11D illustrate multiple views of an embodiment of a quadrangle type temporary vertebral connector element, FIG. 11B being partially transparent and FIG. 11D being a perspective view of an embodiment of a vertebra with two pedicle screw type vertebral fixing elements and a quadrangle vertebral connector.

FIGS. 12A through 12C illustrate multiple views of a polyaxial correcting element.

FIGS. 13A through 13F illustrate multiple views of portions of the distal end of the polyaxial correcting element of FIGS. 12A through 12C for the attachment of the proximal end of a vertebral connector element, FIGS. 13D through 13F being partially transparent.

FIGS. 14A through 14H illustrate an embodiment of polyaxial correcting elements with sagittal inclination to be used in the lordotic spinal regions in multiple conditions of angulation and, FIGS. 14I through 14M, illustrate lateral views of vertebrae in lordosis and their corresponding polyaxial correcting elements in multiple conditions of angulation.

FIGS. 15A through 15D illustrate multiple views of an embodiment of a sagittal positioning correction element to be used with the polyaxial correcting element of FIGS. 12A through 12C and FIGS. 14A through 14H, FIGS. 15B and 15D being partially transparent.

FIG. 16A through 16H illustrate embodiments of sagittal inclination correction elements, FIGS. 16E through 16H being partially transparent, as well as, in FIGS. 16I through 16P, those used with the polyaxial correcting elements of FIGS. 12A through 12C and FIGS. 14A through 14H, FIGS. 16K, 16L, 16O, and 16P being partially transparent and FIGS. 16I through 16L being partial views.

FIGS. 17A through 17L illustrate multiple views of embodiments of frontal inclination correction elements with different angles, FIGS. 17A through 17F being a first angle and FIGS. 17G through 17L being a second angle, FIGS. 17C, 17F, 17I, and 17L being top views, and FIGS. 17D, 17E, 17F, and 17J, 17K, 17L being partially transparent, along with FIGS. 17M through 17O where frontal inclination correction elements are used with a polyaxial correcting element.

FIG. 18 illustrates an embodiment of a closing clamp type correcting force element to be closed over the polyaxial correcting elements.

FIGS. 20A and 20B illustrate multiple views of an embodiment of the corrective force applied with cable(s), in which the fix points in the space are provided by rigid attachments placed at the head and at the bottom of the surgical table and the force is exerted at both free ends of the cable(s).

FIGS. 21A and 21B illustrate multiple views of an embodiment of the corrective force applied with cable(s) in which the fix points in the space are provided by rigid attachments placed at the head and at the bottom of the surgical table and the force is exerted over one end of the cable, being the other end fix.

FIGS. 22A and 22B illustrate multiple views of an embodiment of corrective force applied with cable(s) in which the fix points in the space are provided by rigid attachments placed at the sides of the surgical table and the force is exerted over one or both ends of the cable(s) (shown here forces exerted on one side of the cable(s) only).

FIGS. 23A through 23C illustrate multiple views of an embodiment of a vertebra with all the vertebral elements used for the correction of this invention placed in situ.

DETAILED DESCRIPTION OF THE INVENTION

Figure 4A:
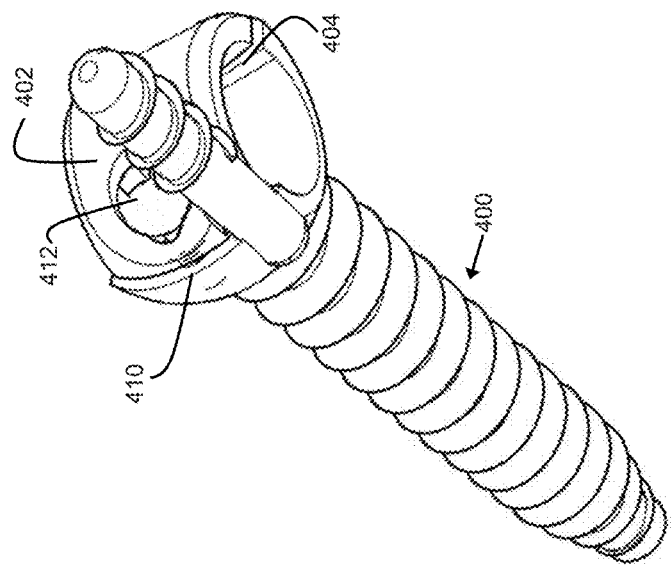
FIGS. 4A through 4D illustrate multiple views of another embodiment of a monoaxial pedicle screw with a hinge type closing cap screw, FIG. 4D being a perspective view.
Figure 4B:
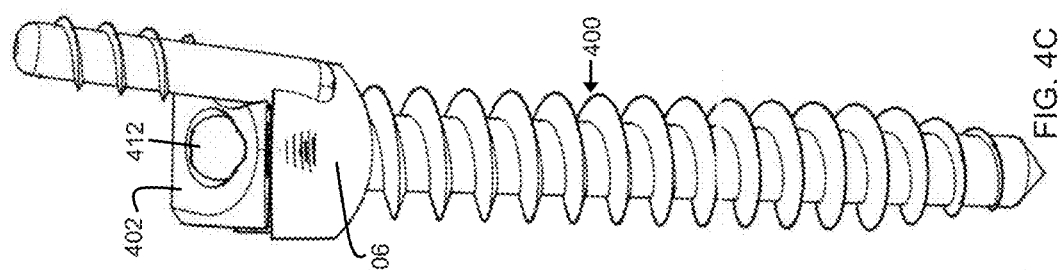
Figure 4C:
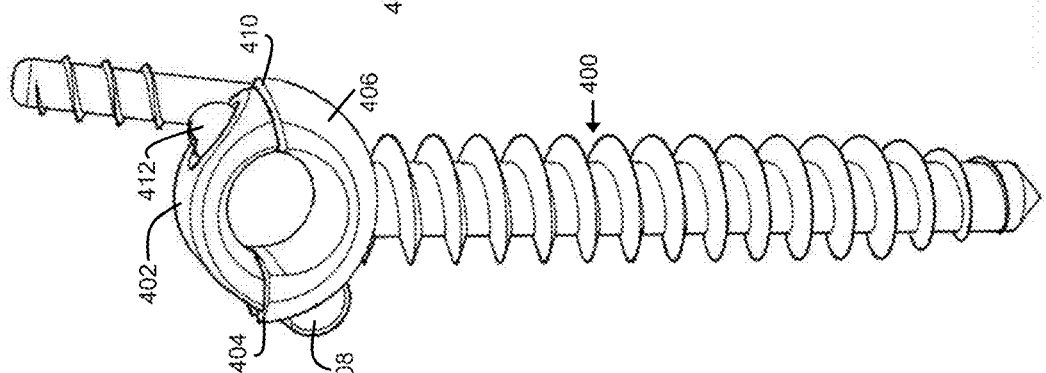
Figure 4D:
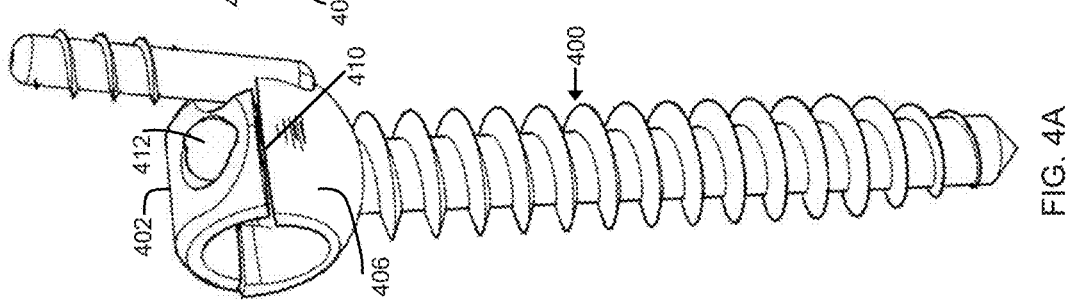

Disclosed herein are requisite tools and methods for an accurate and preplanned three-dimensional correction of the vertebrae in a deformed spine of a patient. Also provided is a means for the definitive fixation of the spine.

Vertebral Fixing Elements

This invention provides vertebral fixing elements that are to be fixed to the vertebrae and hold firmly onto the bone. The vertebral fixing elements employed can be of any of the types commonly used in spine surgery such as pedicle screws, pedicle or laminar hooks, laminar or spinous process wires, cables, staples, loops or any other type of vertebral fixing element.

In one exemplary embodiment, normal pedicle screw type vertebral fixing elements are used to hold onto the vertebra because they provide for a solid fixation of the individual vertebra allowing for its adequate three dimensional space mobilization. The conjoined mobilization of two vertebral pedicle screw elements fixed onto the same vertebra with a permanent vertebral connector allows a solid and secure three-dimensional mobilization of the vertebra in the space. Any combination of two or more vertebral fixing elements holding onto the same vertebra and linked together can be utilized in a similar manner. These vertebral fixing elements joined by a permanent vertebral connector element are included in the definitive spinal fixation with longitudinal spinal fixing rods that are attached and fixed onto the vertebral connector element or the vertebral fixing elements.

In the present invention, common vertebral pedicle screws are modified to be used as vertebral fixing elements used with temporary vertebral connector. In this way two modified pedicle screws holding onto the same vertebra are temporarily joined with a temporary vertebral connector element. These modified pedicle screw type vertebral fixing elements are designed such that when joined by the aforementioned temporary vertebral connector element sufficient space remains so that there is no interference with the longitudinal spinal fixing rods used for definitive spinal fixation of the vertebral fixing elements.

Examples of these modified pedicle screw vertebral fixing element designs include but are not limited to monoaxial pedicle screw(s) as illustrated in FIGS. 1A through 1D, 2A through 2E, 3A through 3E, and 4A through 4D and uniaxial pedicle screws and polyaxial screw(s) as illustrated in FIGS. 5A through 5H and 6A through 6H.

In one possible embodiment comprising a modified monoaxial pedicle screw 100, a stem 102 emerges on one side of the screw head 104 that serves for the attachment and fixation to the temporary vertebral connector, see for example FIGS. 1A through 1D. In one embodiment this stem 102 is solid. The stem emerging on one side of the vertebral fixing element has a terminal end 106 for the attachment and fixation of the temporary vertebral connector element. The terminal end can comprise a variety of forms including for example, spherical or threaded, for the appropriate coupling with the distal end of the temporary vertebral connector elements. Many other forms of attachment between a pedicle screw or any other form of vertebral fixing element, with a temporary vertebral connector not including a stem are also possible as will be apparent to those skilled in this art.

In another possible embodiment the corresponding cap screw 202 of the pedicle screw 200, as shown in FIGS. 2A through 2E, is to be closed over the longitudinal spinal fixing element with a minor turn of the cap screw over the head 206 of the pedicle screw. In this particular embodiment this closing action of the cap screw 202 does not definitively fix the longitudinal spinal fixing rod 216; the rod is firmly fixed with the small central screw 204 placed on the cap screw 202. The screw head 206 in the embodiment shown in FIGS. 2A through 2E has also been modified so that the internal slotted portion 208, used for the accommodation of the rod-type longitudinal spinal fixing element 216, is convex instead of the concave aspect of common pedicle screw heads. The solid convex shape of the slotted part 208 of the head of these monoaxial pedicle screws 200 facilitates the insertion and coupling within the pedicle screws of the longitudinal spinal fixing rods 216 used for the definitive spine fixation, allowing a wider range of relative orientations of the monoaxial pedicle screws as related to the longitudinal spinal fixing rod. In this embodiment (see FIGS. 2A through 2E) the threaded part 210 of the cap screw 202 has a rectangular profile and faces inwards, complementary with the rectangular threads 212 of the head of the monoaxial pedicle screw that are placed on its outer surface 214. In this exemplary embodiment the inner multiple rectangular threads 210 of the cap screw 202 are locked in place with a partial turn of the cap screw over the head 206 of the pedicle screw 200. The central aspect of the cap screw in this embodiment houses an internal screw 204 that is tightened over the rod-type longitudinal spinal fixing element 216. When the cap screw 202 is locked over the pedicle screw head 206 after the longitudinal spinal fixing rod 216 has been introduced in the head of the pedicle screw 200, the inner screw 204 of the cap screw 202 is tightened over the rod-type longitudinal spinal fixing element holding firmly together the rod-type longitudinal spinal fixing element and the pedicle screw vertebral fixing element. The particular embodiment shown in FIGS. 2A through 2E allows about 30 degrees of lateral inclination of the longitudinal spinal fixing rod 216 to each side on the head 206 of the pedicle screw 200 as viewed from above and about 20 degrees of relative orientation up and down on the longitudinal spinal fixing rod as viewed from the lateral aspect, prior to its definitive tightening, greatly facilitating the insertion of the longitudinal spinal fixing rod 216.

In an alternative embodiment, a monoaxial pedicle screw vertebral fixing element is used with temporary vertebral connector elements where the corresponding cap screw is closed over the longitudinal spinal fixing element with a hinge mechanism as shown in FIGS. 3A through 3E and 4A through 4D. The hinged cap screw 302, 402 is first inserted in one of the sides 304, 404 of the head 306, 406 of the pedicle screw 300, 400 in a location intentionally excavated for the insertion of the hinge side 308, 408 of the cap screw and then rotated over this hinge ending and secured onto the other side 310, 410 of the screw head, which can be done for example by means of a mini-screw 312, 412 as shown in FIGS. 3A through 3E and 4A through 4D.

In an alternative embodiment, a uniaxial pedicle screw vertebral fixing element is contemplated to be used with a temporary vertebral connector element.

In an alternative embodiment, polyaxial pedicle screw vertebral fixing elements are used with a temporary vertebral connector element. In one embodiment (FIGS. 5A through 5H), the screw 500 permits about 15 degrees rotation of the mobile part of the pedicle screw head 510 to the left and to the right as viewed from the front and the lateral side and about 12 degrees rotation clockwise and counterclockwise as viewed from above. Alternative embodiments of polyaxial pedicle screws such as the one shown in FIGS. 6A through 6H are envisioned adjusting the degrees of rotation of the design as desired medically.

In exemplary embodiments of polyaxial pedicle screws 500, the protruding terminal ending 508 for the attachment and fixation of the temporary vertebral connectors stems from the spherical head 502 of the pedicle screw and leaves the pedicle screw at a pre-determined angle, traversing through a hole 504 made specifically for this purpose on one side of the mobile part of the head 510 of the polyaxial pedicle screw 500 (FIGS. 5A through 5H).

In alternative embodiments the terminal ending 606 for the attachment and fixation of the temporary vertebral connectors stems from the inferior aspect of the head 602 of the polyaxial pedicle screw 600 at the union 608 between the head of the screw 602 and the longitudinal threaded part of the stem of the screw 600 (FIGS. 6A through 6H).

The pre-determined angle at which the protruding terminal ending (stem) 506, 606 leaves the fixed part of the head 502, 602 of the polyaxial pedicle screw 500, 600 and the precise place/location from which this stem leaves this fixed part of the head 502, 602 of the screw together with the relationship between the width of this protruding terminal ending stem 506, 606 and the size of the hole 504, 604 made on the mobile part 510, 610 of the head of the polyaxial pedicle screw 500, 600, determine the number of degrees of rotation achievable by the polyaxial pedicle screw. As the stem 506, 606 is enlarged (made wider) the hole 504, 604 in the mobile part of the head 510, 610 of the polyaxial screw 500, 600 must be made bigger to achieve the same number of degrees of rotation. However, enlarging this hole 504, 604 makes this mobile part 510, 610 more fragile and prone to breaking. Thus, the relation of the width and direction of this emerging stem 506, 606 in the proximal ending 502, 602 of the polyaxial pedicle screw 500, 600 and the diameter and placement of the hole 504, 604 made on one of the sides of the mobile part of the head 510, 610 of the pedicle screw will determine the range of movement of the polyaxial head 510, 610 of the pedicle screw 500, 600.

These polyaxial pedicle screws 500, 600 facilitate the insertion of the longitudinal spinal fixing rods for the definitive fixation of the vertebrae and the spine.

Many other possible embodiments of terminal endings and attachments for different types of vertebral fixing elements can be designed to be used for a wide variety of permanent or temporary vertebral connector elements, so that the temporary vertebral connector elements firmly hold onto the vertebral fixing elements and the vertebra to which these are fixed to, being the case that any force applied to the vertebral connector element with the intention of mobilizing the vertebra in the space will be directly transmitted to the vertebra itself, and should therefore also be considered under the same scope and spirit of this invention. While one embodiment of the present invention, as described herein, uses two pedicle screw type vertebral fixing elements to provide for a strong hold and fixation onto the vertebra, alternative embodiments are to be contemplated using only one pedicle screw type vertebral fixing element per vertebra, a combination of one pedicle screw type vertebral fixing element with other type of vertebral fixing element or a combination of different vertebral fixing elements holding onto the same vertebra, as will be apparent to those skilled in this art and, so long as the vertebral fixing element(s) provides a solid fixation of the vertebra, that will permit its accurate and three-dimensional mobilization in a similar way as being disclosed in this invention, and are to be considered under the same scope and spirit of this invention.

Vertebral Connector Element

Further provided is a vertebral connector element. This vertebral connector element solidly joins together various or all the vertebral fixing elements that hold onto the same vertebra. The vertebral connector element that links together two or more vertebral fixing elements holding onto the same vertebra acts as a fix point that allows for an accurate three-dimensional mobilization of the vertebra.

The vertebral connector element of this invention can be provided in a permanent embodiment so that it is permanently included in the definitive spinal fixation construct, or in a temporary embodiment, used only temporarily for an adequate mobilization and correction of the vertebrae and the spine and later be removed and not included in the definitive spinal fixation construct.

The embodiments of the vertebral connector elements, whether permanent or temporary, have a dedicated proximal part for the attachment and solid fixation of the polyaxial correcting element (as further described below). In exemplary embodiments shown and described herein this dedicated part of the vertebral connector elements has a spherical form to be housed inside a distal end part of the polyaxial correcting element designated for this purpose. The spherical form of the dedicated part of the vertebral connector element for the attachment of the polyaxial correcting element facilitates the insertion and multidirectional relative orientation in the space of these two elements. This is important for the three-dimensional correction of the vertebra to which the vertebral connector element is attached. In one embodiment, a spherical type of joint union is used; however, any other joint that will serve the same purpose as a Universal joint, a Rzeppa type joint or any other type can be easily designed by those skilled in these arts and should be considered under the same scope and spirit of this invention.

In one embodiment, the permanent vertebral connector element to join together two pedicle screw type vertebral fixing elements is provided in the form of a bent rod as seen in FIGS. 7A through 7D. In the embodiment shown (FIGS. 7A through 7D) the permanent vertebral connector element 700 joins two pedicle screw type vertebral fixing elements 702, 704 (FIG. 7D). The curve of this permanent vertebral connector element in the middle part 706 of the rod 708 facilitates the accommodation of this element between the spinous processes SP of the vertebrae V. A rigid union results between the pedicle screws 702, 704 (or any other vertebral fixing element), and the permanent vertebral connector 700. This vertebral connector element 700 in the form of a bent rod 708 can be of a variety of sizes and lengths in order to adjust for the variable distances between the two pedicle screw type vertebral fixing elements 702, 704 introduced in the vertebrae V and to accommodate for the different sizes of the spinous processes SP of the vertebrae. In alternative embodiments a portion of the vertebral fixing elements 702, 704 are shaped to allow coupling with the vertebral connector 700, where the coupling provides temporary or permanent joining of the vertebral fixing elements with the vertebral connectors.

A permanent vertebral connector element 700 can adopt many other different forms and shapes, whether being a plate, cage, articulating rod or any other form as will be apparent to those skilled in this art and these should be also considered within the scope and spirit of the invention described herein.

As illustrated by FIGS. 8A through 8E, in one embodiment, the temporary vertebral connector element 800 has the form of a compass. As illustrated, each of the legs 802, 804 of the compass type vertebral connector element can be attached to the spherical terminal ending 106, 218, 318, 508 of the protruding stems 102, 220, 314, 506 emerging out of the head of the pedicle screws 104, 206, 306, 502 shown herein 100, 200, 300, 500 or of other type of vertebral fixing elements. Once the legs 802, 804 of these temporary vertebral connector elements 800 are positioned onto the terminal endings 206, 218, 318, 508 of the protruding stems emerging from the pedicle screws heads 104, 206, 306, 502 or any other vertebral fixing elements of the same vertebra, they are tightened and firmly blocked over the vertebral fixing elements. In the particular embodiment shown in FIGS. 8A through 8E, a barrel 806, 808 located inside the legs of the compass 802, 804 descends onto and blocks the spherical ending 106, 218, 318, 508 of the protruding stem 102, 220, 314, 506 emerging from the pedicle screw type vertebral fixing element, (or any other type of vertebral fixing element), resulting in rigid union between the pedicle screws, (or any other vertebral fixing element) and this compass type temporary vertebral connector. The barrels 806, 808 inside the legs 802, 804 of the compass 800 is descended in this exemplary embodiment by the action of a cam shaft mechanism 810, 812 located at the base of the arms 814, 816 of this compass type vertebral connector.

In another embodiment the temporary vertebral connector has an arched form, see for example FIGS. 9A through 9E. A double polyaxial joint 1000, shown in FIGS. 10A through 10F, is used to attach and fix the spherical ending 106, 218, 318, 508 of the protruding stem 102, 220, 314, 506 emerging from the vertebral fixing element 100, 200, 300, 500. This double polyaxial joint of FIGS. 10A through 10F is tightened with the help of a screw 1006 that blocks the joint over the legs 902, 904 of the arch type temporary vertebral connector 900. In this particular embodiment of an arch type temporary vertebral connector 900, this same screw 1006 also blocks the spherical ending 106, 218, 318, 508 of the protruding stem 106, 218, 318, 508 emerging from the vertebral fixing element. Blocking is done by means of a reverse thread nut 1008 placed over this tightening screw 1006 in such a way that the nut increases its distance from the double polyaxial joint 1000 while the screw 1006 is advanced and closes the double polyaxial joint over the spherical ending 106, 218, 318, 508 of the protruding stem 106, 218, 318, 508 emerging from the vertebral fixing element by means of a strong cable 1010 that encircles the distal hinged part 1012 of the double polyaxial joint as seen in FIGS. 10A through 10F. FIGS. 10A through 10C provide an external appearance of a double polyaxial joint 1000 including 10A: 1/ a view of a double polyaxial joint without the screw 1006 and nut 1008; 10B: 2/ a view of the screw 1006 and the tightening cable 1010; 10C: 3/ a view of a double polyaxial joint 1000 with the screw 1006 tightened, thereby simultaneously compressing the two spherical parts 1014, 1016 of the joint, and the cable 1010 that is tensioned while the screw 1006 is advanced, so that the inferior part of the double polyaxial joint 1016 closes over the spherical end part 106, 218, 318, 508 of the protruding stems 106, 218, 318, 508 that emerges from the vertebral fixing element.

In another embodiment as illustrated by FIGS. 11A through 11D, the vertebral connector element 1100 has a quadrilateral form. Here, the temporary vertebral connector element 1100 is formed by the quadrangular construct of rods 1102, 1104 attached to the protruding ending stems 1106, 1108 emerging from the vertebral fixing element 1112, 1114 and a transverse rod 1110 that links solidly the rods 1102, 1104 attached to the vertebral fixing elements 1112, 1114. In this particular embodiment, the threaded ending of the protruding ending stem 1106, 1108 emerging from the vertebral fixing element 1112, 1114 is joined to the rods 1102, 1104 of the quadrangle type temporary vertebral connector 1100 by tightening the threaded ending 1106, 1108 inside the internal threaded portion 1116, 1118 of the distal end of the rods 1102, 1104 of the quadrilateral type temporary vertebral connector element construct 1100.

Once the temporary vertebral connector element(s) are firmly attached to the pedicle screws of the same vertebra or to any combination of vertebral fixing elements holding onto the same vertebra, the forces applied to the temporary vertebral connector element will be transmitted to the vertebra to which the vertebral fixing elements are attached.

Many other possible embodiments of terminal endings and attachments for different types of vertebral fixing elements can be designed to be used for a wide variety of permanent or temporary vertebral connector elements, so that the vertebral connector elements firmly hold onto the vertebral fixing elements and the vertebra to which these are fixed to, being the case that any force applied to the vertebral connector element with the intention of mobilizing the vertebra in the space will be directly transmitted to the vertebra itself, and should therefore also be considered under the same scope and spirit of this invention Vertebral Correcting Element(s)

A polyaxial correcting element is attached and fixed to a vertebral connector element. In one embodiment the attachment is done between the distal end part joint system and fixation of the polyaxial correcting element to the proximal end part joint system and fixation of a vertebral connector element (either temporary or permanent). For the correct alignment of the vertebral elements in the frontal plane the polyaxial correcting elements are used.

A particular embodiment of a polyaxial correcting elements is illustrated in FIGS. 12A through 12C.

The polyaxial correcting element that is connected to the vertebral connector element is to be solidly attached to the permanent or temporary vertebral connector element in a way such that a force applied over the polyaxial correcting element will be transmitted to the vertebra by means of the vertebral connector element and the vertebral fixing elements to which this last is attached.

In another possible embodiment the polyaxial correcting element can be attached directly to the vertebral fixing elements in the desired position for a pre-planned three-dimensional mobilization of the vertebra. This can be done whether these polyaxial correcting elements are only placed on the vertebral fixing element placed on one side of the vertebra or are placed on all the vertebral fixing elements attached to a vertebra.

One possible embodiment of a polyaxial correcting element 1200 has a cylindrical structure that is slotted 1202 in its central part through a significant extent of its length L, see for example FIGS. 12A through 12C. The polyaxial correcting elements can have a wide variety of forms, and lengths and transverse sections. In the particular embodiment shown in FIGS. 12A through 12C the polyaxial correcting element 1200 has a cylindrical form with a small diameter D and a length L suitable for the easy mobilization of the vertebra by means of a light force exerted directly at the free ending 1204 of the polyaxial correcting element 1200 or at a closer distance along the polyaxial correcting element 1200 from the vertebra to where it is attached.

The polyaxial correcting element 1200 features a distal end part 1300 designed for housing the proximal end of the vertebral connector element in a wide range of spatial orientations. Portions of an embodiment of the distal end part 1300 of the polyaxial correcting element of FIGS. 12A through 12C are shown in FIGS. 13A through 13F. The distal ending 1300 of the polyaxial correcting element 1200 permits inclination and rotation of the polyaxial correcting element in a wide range of degrees over the proximal end part of the vertebral connector element in such a way that the polyaxial correcting element 1200 can be oriented easily as desired in relation to the vertebral connector element and in relation to the vertebra to which it is fixed.

As the vertebrae of the lumbar region of the normal subjects are disposed in a concave shape as viewed from the back, the use of a long stemmed embodiment of polyaxial corrector elements 1200 can make it difficult for these polyaxial correcting elements to be realigned into the same sagittal plane if the polyaxial correcting elements are initially aligned parallel as viewed from the lateral side and the lumbar spinal lordosis (concavity) is to be restored. This difficulty can be overcome through variation and the change of angle of the placement of the polyaxial correcting elements 1200 in the vertebral correcting elements to ensure there is adequate space when the lumbar lordosis of the spine is reconstructed.

In another possible embodiment this problem is solved by the use of polyaxial correcting elements 1200, 1400B, 1400C, 1400D, 1400E, 1400F, 1400G, 1400H that have been designed with a distal end 1402B, 1402C, 1402D, 1402E, 1402F, 1402G, 1402H having different angulations as viewed from the lateral side. Similarly the angulation at the distal end of the polyaxial correcting elements can be adjusted via a rotating and locking mechanism. FIGS. 14A through 14H illustrate an embodiment of polyaxial correcting elements with sagittal inclination in increments of seven degrees to be used in the lordotic spinal regions and FIG. 14I a lateral view of five vertebra in lordosis and their corresponding polyaxial correcting elements (vertebral fixing elements and vertebral connectors are not shown but represented by dotted lines).

In the embodiments of angled polyaxial correcting elements of FIGS. 14A through 14H the increments of the angle of the distal end 1402B, 1402C, 1402D, 1402E, 1402F, 1402G, 1402H have been arbitrarily established to be seven degrees, but any other increment of degrees is possible to accommodate for the size and expected lordosis of the spine of the subject requiring treatment.

When the polyaxial correcting element 1200, 1400B, 1400C, 1400D, 1400E, 1400F, 1400G, 1400H is firmly fixed to the vertebral connector element, any force applied to the polyaxial correcting element will be transmitted to the vertebra where it is attached. As previously mentioned, in one embodiment, the connection between the distal end 1300 of the polyaxial correcting element 1200 and the proximal end or attachment structure of a vertebral connector element 720, 830, 930, 1130 is done by means of a spherical joint 721, 821, 931, 1131 that allows for forward and backwards inclination, lateral inclination to both sides, and complete rotation of the polyaxial correcting element 1200 as related to the proximal ending 730, 830, 930, 1130 or attachment structure of the vertebral connector element 700, 800, 900, 1100. However, many other forms of multidirectional joint between a polyaxial correcting element and a vertebral connector element that will allow multi-axial or polyaxial mobilization, such as a Universal joint, a Rzeppa joint or any other joint can be used and should also be considered within the scope and spirit of this invention.

Included within the correcting elements of this invention are other aligning elements. These other aligning elements are to be placed along, over or inside the structure of the polyaxial correcting elements 1200, 1400B, 1400C, 1400D, 1400E, 1400F, 1400G, 1400H These aligning elements are designed to provide the means for the adequate alignment of the vertebrae. For the correct alignment of the vertebra as viewed in the sagittal plane, the sagittal positioning correction elements are used. For the correct inclination of the vertebra in the sagittal plane, the sagittal inclination correction elements are used. For the correct inclination of the vertebra in the frontal plane, the frontal inclination correction elements are used. These elements are designed in a way as to be easily placed along, over or inside the length of the polyaxial correcting element and their adequate positioning will promote, with the use of a correcting force element(s), the desired and precise correction of the vertebra and the spine that this invention discloses.

A sagittal positioning correction element can be used with a polyaxial correcting element 1200. The sagittal positioning correcting elements are placed and fixed at a desired distance from the proximal 1204 or distal end 1300 of the polyaxial correcting element 1200 as determined and planned before surgery. The placement of the sagittal positioning correction elements can be modified intra-operatively if considered necessary or appropriate. These sagittal positioning correction elements will promote the relative forward and backwards displacement of the vertebra to which the polyaxial correcting element is fixed to in relation to its neighboring vertebrae in the sagittal plane. FIGS. 15A through 15D illustrate a polyaxial correcting element 1200 wherein the sagittal positioning correction elements are constituted by the two nuts and bolts 1502, 1504 that can be moved and placed at different distances along the length of the polyaxial correcting element 1200.

The sagittal inclination correction elements 1600, 1602, 1604, 1606 are placed and fixed at a desired distance from the proximal 1204 or distal end 1300 of the polyaxial correcting element 1200, as determined and planned before surgery. The position of the sagittal inclination correction elements 1600, 1602, 1604, 1606 can be modified intra-operatively if considered necessary or appropriate. This sagittal inclination correction element 1600, 1602, 1604, 1606 will promote the relative sagittal inclination of the vertebra to which the polyaxial correcting element 1200 is fixed to in relation to its neighboring vertebrae in the sagittal plane. FIGS. 16A through 16P illustrate some particular embodiments of sagittal inclination correction elements 1600, 1602, 1604, 1606 of different sizes and shapes to be used with the polyaxial correcting elements such as those depicted in FIGS. 12A through 12C and 14A through 14H. It is noted that the present invention allows for planning of sizing and placement of sagittal inclination correction elements before surgery. Further, the sagittal inclination of the vertebrae is not done at the end of the correction in the frontal plane alignment but rather in a smooth and continuous way at the same time as the correction of the vertebrae in other planes.

A frontal inclination correction element can be used with the polyaxial correcting element. The frontal inclination correction elements are placed and fixed along the polyaxial correcting elements. In varying embodiments, the frontal inclination correction elements 1/are placed in line with the sagittal positioning correction element; 2/ are placed at a different distance in the polyaxial correcting element; 3/ are designed as a unique correcting element 4/are designed forming a unique element with the sagittal positioning correction element and/or 5/ are designed forming a unique element with the sagittal inclination correction element. The placement of the frontal inclination correction elements can be modified intra-operatively if considered necessary or appropriate. These frontal inclination correction elements promote the restoration of the normal frontal inclination of the vertebrae. FIGS. 17A through 17O illustrate some embodiments of frontal inclination correction element 1700 to be used for example with the polyaxial correcting elements of FIGS. 12A through 12C and 14A through 14H.

A correcting force element(s) (FIGS. 18, 19A and 19B) can be used with the polyaxial correcting elements, sagittal positioning correction elements, sagittal inclination correction elements and frontal inclination correction elements.

In one embodiment, the correcting force is a cable tensioning system 1900, 1902. This embodiment can be composed of one or more cables, and can comprise a wide range of forms of providing corrective force as designed by one skilled in this art. In alternate exemplary embodiments such means of applying correcting force can be flexible or rigid, and/or linked, straight, curved or precontoured to a definitive and expected spine curvature. Similarly, the correcting mechanism can be acting in a variety of ways including but not limited to cable tensioning system 1900, 1902, lateral compression system by lateral compressing or sliding rods, lateral closing system by lateral closing clamp(s) 1800, lateral compression articulating rod system, lateral compression articulating clamps system, and combinations thereof. In alternative embodiments the alignment of the polyaxial correcting elements can be promoted by forces acting in a more anterior-posterior direction using the same principles of compression, closing or tensioning of correcting force elements, each one of which will have its particular embodiments of polyaxial correcting elements, sagittal positioning correction elements, sagittal inclination correction elements and frontal inclination correction elements, which are also to be considered within the aims and scope of this invention when used in a correction maneuver with the same purpose.

Figure 19A:
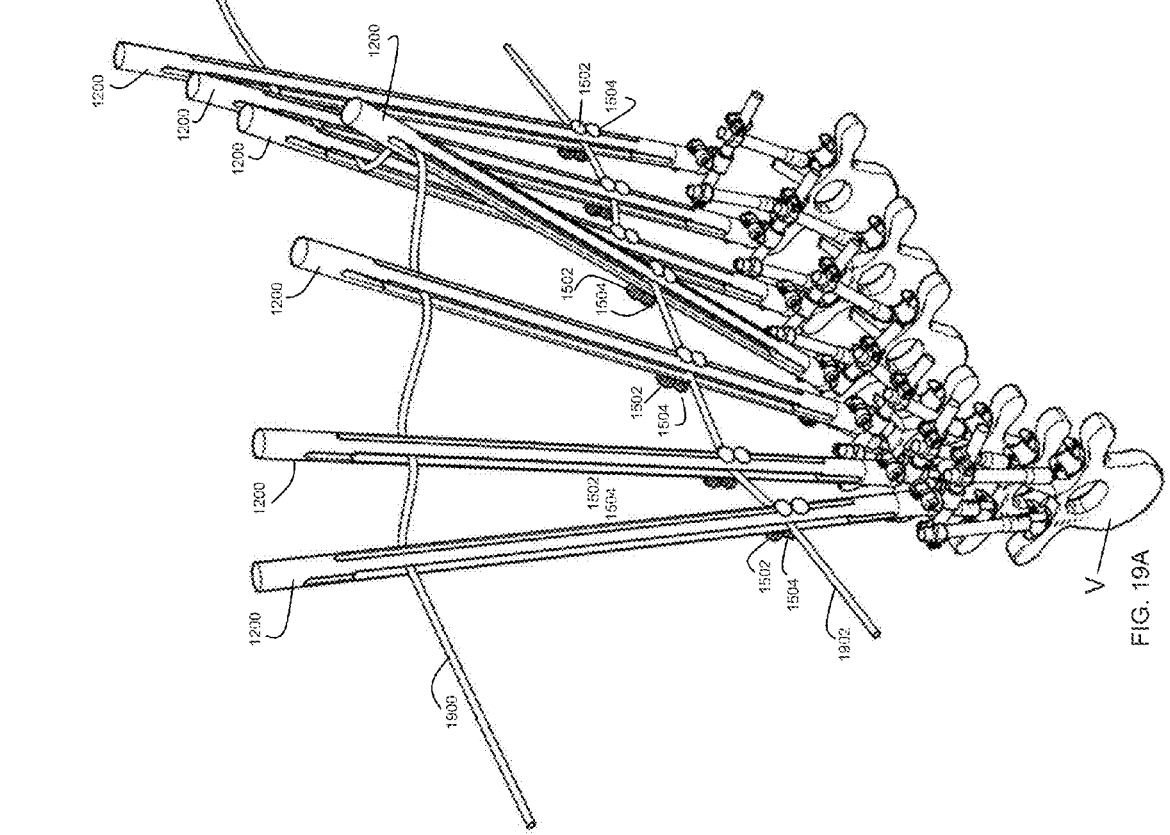
FIGS. 19A and 19B illustrate multiple views of an embodiment of corrective force formed by a two-cable structure to be used with the polyaxial correcting elements.
Figure 19B:
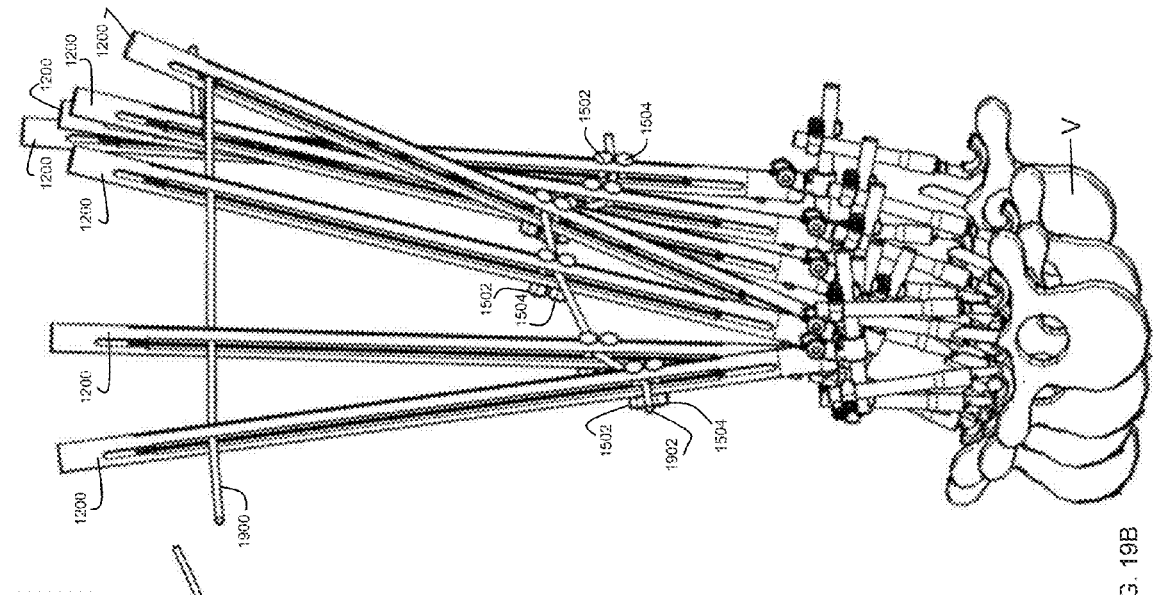

FIGS. 19A and 19B illustrate an embodiment of a means for providing corrective force formed by a two-cable structure 1900, 1902 to be used for example with the polyaxial correcting elements of FIGS. 12A through 12C and 14A through 14H and correcting elements of FIG. 15A through 15D (sagittal positioning correcting elements), 16A through 16P (sagittal inclination correction elements), and 17A through 17O (frontal inclination correction element); (sagittal inclination correction elements of FIGS. 16A through 16P and frontal inclination correction elements of FIGS. 17A through 17O are not shown to facilitate visualization of the cables). In practice, as a tension force is progressively applied on the extremities of the cable(s) 1900, 1902 that traverse the polyaxial correcting elements 1200 and sagittal positioning elements 1502, 1504 of FIGS. 19A and 19B, the polyaxial correcting elements are physically realigned into the same sagittal plane. The force applied on the cable(s) 1900, 1902 is transmitted finally to the vertebra V to which the polyaxial correcting elements 1200 are affixed, promoting the progressive and adequate mobilization of the vertebrae until a final desired state is obtained as pre-planned. More than one tensioning cables 1902 can be utilized in this embodiment. For example, a second tensioning cable 1900 utilized through the polyaxial correcting element, as seen in FIGS. 19A and 19B, helps and facilitates the adequate and progressive mobilization and correction of the malpositioned vertebrae.

Sagittal positioning correction elements 1502, 1504 can be inserted and fixed along the length of the polyaxial correcting element 1200 at a desired distance from its distal 1300 or proximal end 1204. These sagittal positioning correction elements can be designed in-situ along the polyaxial correcting element or can be easily introduced and moved along the polyaxial correcting element to be firmly fixed at a desired and planned position. In one embodiment, and as previously described, these sagittal positioning correction elements are simply bolts and nuts 1502, 1504 that can be placed along the length of the slotted 1202 cylindrical structure of the embodiment of the polyaxial correcting element 1200 such as shown in FIGS. 15A through 15D and fixed where desired. The distance from the proximal or distal end of the polyaxial correcting element at which the sagittal positioning correction element is placed and fixed will influence the sagittal plane correction of the vertebra. It is the relative difference of distances at which the sagittal positioning correction elements 1502, 1504 are fixed along the length of the polyaxial correcting elements 1200, attached to the different vertebrae that are being corrected, that will determine the final disposition of the vertebrae in the sagittal plane once all the polyaxial correcting elements 1200 are aligned in the same sagittal plane by the force exerted with the help of the correcting force element(s) 1900, 1902 and all the sagittal positioning correction elements 1502, 1504 of the different polyaxial correcting elements 1200 are hence forced to be realigned into a straight line. The purpose of the sagittal positioning correction elements 1502, 1504 is thus to promote the final and desired positioning of the vertebrae in the sagittal plane as planned by the preoperative evaluation and analysis of the spine being corrected. Many shapes and forms of sagittal positioning correction elements to be placed inside, along or over a polyaxial correcting element and for the correction of the vertebra in the sagittal plane of the space can be designed as will be apparent to those skilled in this art and should be also considered under the same spirit and scope of this invention when used with this intention.

The realignment into the same sagittal plane of the polyaxial correcting elements 1200 fixed to the vertebrae, by the action of the correcting force element 1900, 1902, with the use of the sagittal inclination correction elements 1600, 1602, 1604, 1606 promotes and forces the desired inclination in the sagittal plane of the vertebra to which the polyaxial correcting element 1200 is attached. The superior or inferior angular mobilization of the polyaxial correcting elements 1200 as viewed in the sagittal plane is promoted by the selective and precise placement and fixation of the sagittal inclination correction elements 1600, 1602, 1604, 1606 along the length of the polyaxial correcting elements. The sagittal inclination correction elements 1600, 1602, 1604, 1606 induce the relative separation and inclination in the sagittal plane of the polyaxial correcting elements 1200 when effectively the polyaxial correcting elements 1200 are forced to be realigned into the same sagittal plane by the effect of the forces procured by the correcting force element(s) 1900 1902. In one possible embodiment, as seen in FIGS. 16A through 16P, the sagittal inclination correction elements 1600, 1602, 1604, 1606 are fixed to the polyaxial correcting element 1200 with a screw and nut mechanism, have a torus 1600 or half-torus shape 1602, 1604, 1606, and/or have different sizes to facilitate the relative motion of the polyaxial correcting elements along them as they are being realigned into the same sagittal plane by the action of the forces procured by the correcting force element(s). This sagittal inclination correction element 1600, 1602, 1604, 1606 is devised to be easily placed along the length of the polyaxial correcting element 1200 and firmly fixed to it at a pre-determined and planned distance. However, many other forms and shapes of sagittal inclination correction elements having a similar function are possible as will be easily apparent to those skilled in this art and are to be included within the spirit and scope of this invention.

The realignment of the polyaxial correcting elements 1200 fixed to the vertebrae with the use of the frontal inclination correction elements 1700 promotes and forces the desired inclination in the frontal plane of the vertebra to which the polyaxial correcting element 1200 is attached. This correction and definitive frontal inclination of the vertebrae is achieved by means of the rotation in the frontal plane of the polyaxial correcting elements 1200 during the correction process, facilitated with the help of the correcting force element(s) 1900, 1902 acting along the polyaxial correcting elements 1200 and the frontal inclination correction elements 1700. The correction is promoted by the selective and precise placement and fixation of the frontal inclination correction elements 1700 along the length of the polyaxial correcting elements 1200. The frontal inclination correction elements 1700 induce the rotation in the frontal plane of the polyaxial correcting elements 1200 clockwise or counter clockwise when these last are forced to be realigned into the same sagittal plane by the effect of the forces procured by the correcting force element(s) 1900, 1902. In one possible embodiment, as seen in FIGS. 17A through 17O, the frontal inclination correction elements 1700, 1710, 1720 have a double-wall shape 1702, 1704, 1722, 1724, and 1712, 1714 that permits the passage of the cables of the correcting force element embodiment herein described 1900, 1902. The frontal inclination correction element 1700, 1710, 1720 is devised to be easily placed along the length of the polyaxial correcting element 1200 and firmly fixed to it at a pre-determined and planned distance and in the particular embodiment shown in FIGS. 17A through 17O, this is done by means of a screw and nut mechanism 1706. However, many other forms and shapes of frontal inclination correction elements having a similar function are possible as will be easily apparent to those skilled in this art and are to be included within the spirit and scope of this invention.

A correcting force element(s) 1900, 1902 can act upon the polyaxial correcting elements 1200, 1400B, 1400C, 1400D, 1400E, 1400F, 1400G, 1400H, the sagittal positioning correction elements 1502, 1504, the sagittal inclination correction elements 1600, 1602, 1604, 1606 and the frontal inclination correction elements 1700, 1710, 1720 to promote the alignment of the vertebra as planned in advance. In one embodiment, as seen in FIGS. 19A through 19B, this correcting force element is formed by two flexible and resistant cable(s) 1900, 1902 of a metal alloy or any other stress/strain resistant material that can be easily introduced along the polyaxial correcting elements 1200 and through the sagittal positioning correction elements 1502, 1504, the sagittal inclination correction elements 1600, 1602, 1604, 1606 (not shown here) and the frontal inclination correction elements 1700, 1710, 1720 (not shown here) attached to the polyaxial correcting elements 1200. This correcting force element(s) 1900, 1902 realign and mobilize the polyaxial correcting elements 1200 and the vertebrae V to which these are attached to correct and modify the shape of the spine.

By straightening the cable(s) of the correcting force element(s) 1900, 1902 embodiment such as shown in FIGS. 19A through 19B, the polyaxial correcting elements 1200 are progressively moved into the same sagittal correction plane by the medial force acting along the length of the polyaxial correcting element 1200. The force exerted along the polyaxial correcting elements 1200 by the tensioning of the cable(s) 1900, 1902 is guided by the presence of the sagittal positioning correction elements 1502, 1504, the sagittal inclination correction elements 1600, 1602, 1604, 1606 and the frontal inclination correction elements 1700, 1710, 1720, and decomposed and transformed into medial-lateral displacement, anterior-posterior displacement, and rotation in the frontal plane, the sagittal plane and the axial plane of the polyaxial correcting elements 1200, mobilizing and realigning at the same time the vertebrae V to which these polyaxial correcting elements 1200 are attached.

In another embodiment of this invention employing tensioning cables, the correction maneuver can be facilitated by the alternating and progressive tightened of the different cables employed.

In alternative embodiments varying means for applying corrective force can also be used, whether employed alone or in combination with other types of means for applying corrective force, in order to facilitate the correction maneuver upon the polyaxial correcting elements 1200.

In another possible embodiment using cables as a means for applying corrective force, the force applied over the polyaxial correcting elements and their correcting elements attached can be exerted in an individualized manner for each vertebra to be corrected. In this sense, and in an embodiment using cables for correcting the spine deformity, one or more differentiated tensioning cable(s) is used for each vertebra to be corrected, and the direction of the tensioning cables acting over the polyaxial correcting elements, the sagittal positioning correction elements, the sagittal inclination correction elements and the frontal inclination correction elements could be exerted, for each particular polyaxial correcting element, through the same direction or through different directions.

In another possible embodiment with multiple tensioning cables a measuring tensiometer can be attached to each of the cables to measure the force used to correct each vertebra and in this way determine the most appropriate sequence of correction of the polyaxial correcting elements and the vertebrae.

In another possible embodiment using multiple cables, an electrical or other power driven mechanism can be used where the tensioning of one or more of the tensioning cables can be programmed to correct the deformity in a pre-determined way. In this fashion, the tensioning of each cable can be provided by selectable parameters such as, time to final tensioning of the cable, time to final length correction of the cable, maximum tensioning force applied to the cable, increments of tension force per time unit, length of the cable being collected by the power driven mechanism per unit of time, angle of the polyaxial correcting element being corrected per unit of time and any combination of these parameters so that the values applied to these parameter can vary as a linear or non linear function dependent on the time or as a function dependent on any other of the above mentioned parameters. So for example, where an electrical motor is used as the power mechanism for the tensioning of the cables, the tensioning can be programmed to include for example, the duration of the tensioning, the maximum force to be applied to each of the cables of the correcting element, the amount of correction (as defined by length of cable collected) as a function of time. Such programming would include variable programming allowing for different modes of correction.

Exemplary embodiments of the direction of the forces of an embodiment of a means for providing corrective force using cable(s) are provided in FIGS. 20A, 20B, FIGS. 21A, 21B, and FIGS. 22A, 22B. Effectively two points in space 2000, 2002, 2100, 2102 and 2200 2202 are fixed for each cable 1900, 1902 to be tensioned and the line between these two points in space will coincide with the desired sagittal plane alignment of the spine deformity correction.

In the correction method herein disclosed, the correct coronal straight alignment of the vertebrae is determined by the realignment of the polyaxial correcting elements into the same sagittal plane, which is promoted by the straightening of the cables that can be supplemented by the straightening force of another means for providing corrective force superimposed over the polyaxial correcting elements to further facilitate the sagittal realignment of the polyaxial correcting elements if necessary. In one possible embodiment a clamp 1800, such as illustrated in FIG. 18, can be used in combination with the cable type embodiment 1900, 1902 to facilitate the realignment of the polyaxial correcting elements 1200.

An embodiment of a vertebra V with two pedicle screw type vertebral fixing elements 1112, 1114, a quadrangle temporary vertebral connector element 1100, a polyaxial correcting element 1200, and sagittal positioning correction elements 1502, 1504, sagittal inclination correction elements 1600 and frontal inclination correction elements 1720 placed along the polyaxial correcting element 1200 can be seen in FIGS. 23A through 23C in conjunction with the cables 1900, 1902 of the cable type means for providing connective force traversing the correcting elements used to mobilize the vertebra V in the three-dimensional space.

Proper planning and placement of the polyaxial correcting elements over the vertebral connector elements is important to obtain a correct alignment of the vertebrae and the spine in the frontal plane.

The adequate correction of the axial malalignment of each individual vertebrae rests upon the inclination at which the polyaxial correcting element is attached and fixed over the vertebral correcting element as viewed on the axial plane.

Similarly, the correct alignment of the vertebrae and the whole spine in an adequate sagittal contour rests upon the correct planning and placement of the sagittal positioning correction elements over the polyaxial correcting elements.

In a similar way the final inclination of each individual vertebrae as viewed in the sagittal plane rests upon the correct planning and adequate placement of the sagittal inclination correction elements along the polyaxial correcting elements.

An important factor for a correct final inclination of each individual vertebrae as viewed in the frontal plane rests upon the correct planning and adequate placement of the frontal inclination correction elements along the polyaxial correcting elements.

In the invention herein described, the definitive spinal fixation is done after the desired correction of the spine is achieved by the correction method and apparatuses described above. The definitive spinal fixation of the corrected spine can be done with commonly used rod-type longitudinal spinal fixing elements fixed to the vertebral fixing elements or fixed to the permanent vertebral connector elements if this construct is chosen for the correction of the spine and the definitive fixation. In a preferred embodiment this longitudinal spinal fixing element will have the form of a rod and will be used with pedicle screw type vertebral fixing elements, but a plate or any other form of longitudinal spinal fixing element can also be used.

The vertebral fixing elements, the permanent vertebral connector and the longitudinal spinal fixing element can comprise for example a biocompatible rigid alloy such as are titanium, stainless steel or cobalt-chrome alloys, but other inert or biocompatible materials like memory-shape alloys, nanostructure materials or any other inert material whether rigid or flexible that is suitable for the definitive spinal fixation can be used and shall also be included within the spirit and scope of this invention.

In one embodiment, the union between the longitudinal spinal fixing element and the permanent vertebral connector elements or the vertebral fixing elements is rigid, does not allow for motion between these elements and has a low profile so as not to protrude under the skin of the patients' back; however, other possible embodiments of union mechanisms between vertebral fixing elements or permanent vertebral connector and longitudinal spinal fixing elements will come to the mind of those skilled in this art where this union can be flexible, semi-rigid or permit one or more degrees of freedom between the longitudinal spinal fixing element and the vertebral fixing element or the permanent vertebral connector that will allow for a certain degrees of mobilization, and shall be included under the same spirit and scope of this invention.

In the embodiments where permanent vertebral connector elements are used for the correction of the spine, one or more longitudinal spinal fixing elements can be used for the definitive fixation of the spine.

In one possible embodiment of definitive fixation between a permanent vertebral connector element and a rod-type longitudinal spinal fixing element that is rigidly fixed, the union between these elements is done by means of a nut and screw with a steel cable that is tightened around the longitudinal spinal fixing element and the vertebral connector element in such a way that as the screw is turned over the nut, it presses against the longitudinal spinal fixing element while the cable around the permanent vertebral connector is at the same time tightened. However, a wide variety of other possible embodiments for the fixation between a permanent vertebral connector element and a longitudinal spinal fixing element can be designed, whether tightened, fastened, screwed or joined by any other mean, as will be apparent to those skilled in this art and are also to be included under the same spirit and scope of this invention.

In the embodiments where temporary vertebral connector elements are used for the correction of the spine, two longitudinal spinal fixing elements will commonly be attached to the vertebral fixing elements for the definitive fixation of the spine, each one of the longitudinal spinal fixing elements on each side of the spine. However, one may choose to selectively fix only the vertebral fixing elements on one side of the spine or a variable number of the vertebral fixing elements on one or both sides of the spine.

The type of connections used between the longitudinal spinal fixing elements and the permanent vertebral connector elements or between the vertebral fixing elements and the longitudinal spinal fixing elements can vary between different embodiment constructs or be different within the same construct embodiment so as to rigidly fix the segment of the spine being corrected or to allow for some degrees of motion of the vertebrae in some parts of the construct while definitively and rigidly fixing other vertebrae of the spine being treated.

In one embodiment for the fixation of a spinal segment, only one longitudinal spinal fixing element joins two vertebrae together either through permanent vertebral connector elements or by means of the vertebral fixing elements. However, in an alternative embodiment, all the vertebrae of the spine are fixed to longitudinal spinal fixing elements via permanent vertebral connector elements or vertebral fixing elements, including as high as the upper cervical vertebrae and the base of the skull and as low as the sacrum and the pelvis into the final construct.

In one embodiment two longitudinal spinal fixing elements are used for the definitive fixation of the vertebral column but in other embodiments the construct can have only one longitudinal spinal fixing element capable of bearing all the loads and stresses of the spine. In more complex constructs more than two longitudinal spinal fixing elements are employed and fixed to permanent vertebral connectors.

Once the definitive spinal fixation has been done, all the temporary elements used for the correction of the spine deformity are removed and the protruding stems of the vertebral fixing elements shown in the particular embodiments of this invention can be cut and removed if desired.

After the correction and fixation of the spine has been achieved an arthrodesis and closure of the surgical can then be done in a standard fashion.

Not only the embodiments described and shown in this disclosure are possible but many other forms and shapes of vertebral fixing elements, vertebral connector elements, polyaxial correcting elements, sagittal positioning correction elements, sagittal inclination correction elements, frontal inclination correction elements and correcting force elements can be devised as well as the joints between these elements that can be designed and used so as to accomplish an accurate and pre-planned three-dimensional mobilization and correction of the vertebrae in a similar controlled and progressive way as this disclosure describes and in this way these embodiments are also intended to be considered under the same scope and spirit of the present invention.

The three-dimensional correction method of the spine and the fixation system herein disclosed makes it ideal for any situation where an accurate correction and a definitive fixation of the spine is desired.

This invention is therefore ideal for the correction and fixation of the most severe deformities of the spine whether congenital, idiopathic, acquired, degenerative or due to any other cause. In these severe deformity cases a detailed pre-surgical analysis and evaluation of the spine malalignment is mandatory if an accurate correction of this malalignment is to be expected. The coronal and sagittal misalignment of the vertebrae are to be considered as well as the coronal inclination, sagittal inclination and axial rotation of each vertebrae involved in the segment of the spine to be corrected, as the magnitude of these misalignments will determine the correct positioning of all the correcting elements described in this disclosure that will achieve a desired and pre-planed correction of the deformity of the spine.

This invention is suitable for the fixation of acute, subacute and chronic vertebral fractures whether fixation is to be done either in situ or after correction of the deformity of the spine has been done.

This invention is suitable for the correction and fixation of sagittal deformities of the spine such as lumbar or cervical kyphosis, thoracic hyperkyphosis, lumbosacral anterolisthesis as well as the correction and fixation of vertebral listhesis where a vertebra slides over the one placed immediately below or above.

The rigidity and strength of the spinal fixation achieved with this invention makes it also ideal for the vertebral fixation of tumoral or degenerative processes of the spine that hinder mechanical stability and pose a thread to the neurological integrity of the patient.

Figure 24:
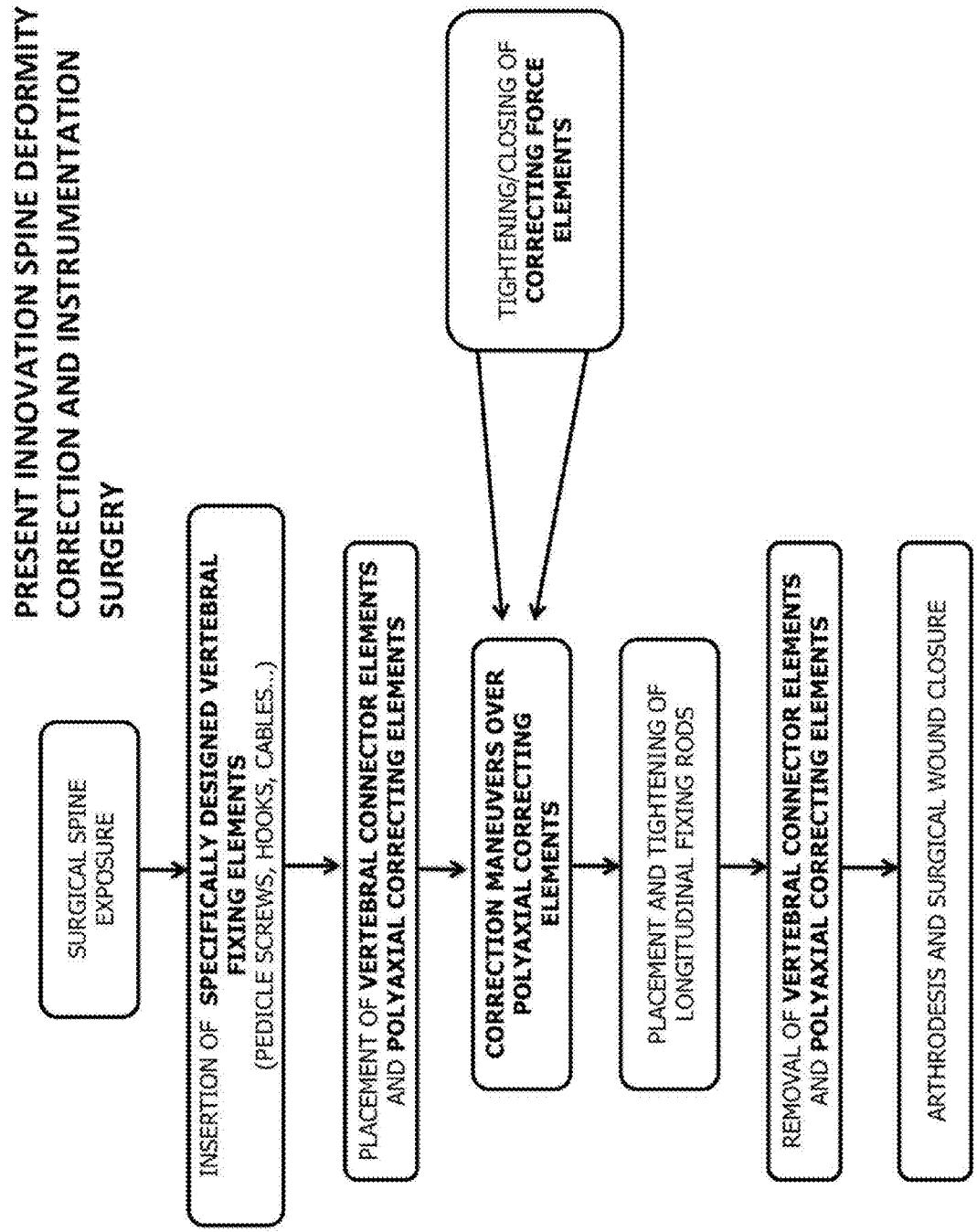
FIG. 24 illustrates a scheme of the process of the present invention used for the correction and fixation of a spine deformity using the instrumentation of this invention.
Figure 25:
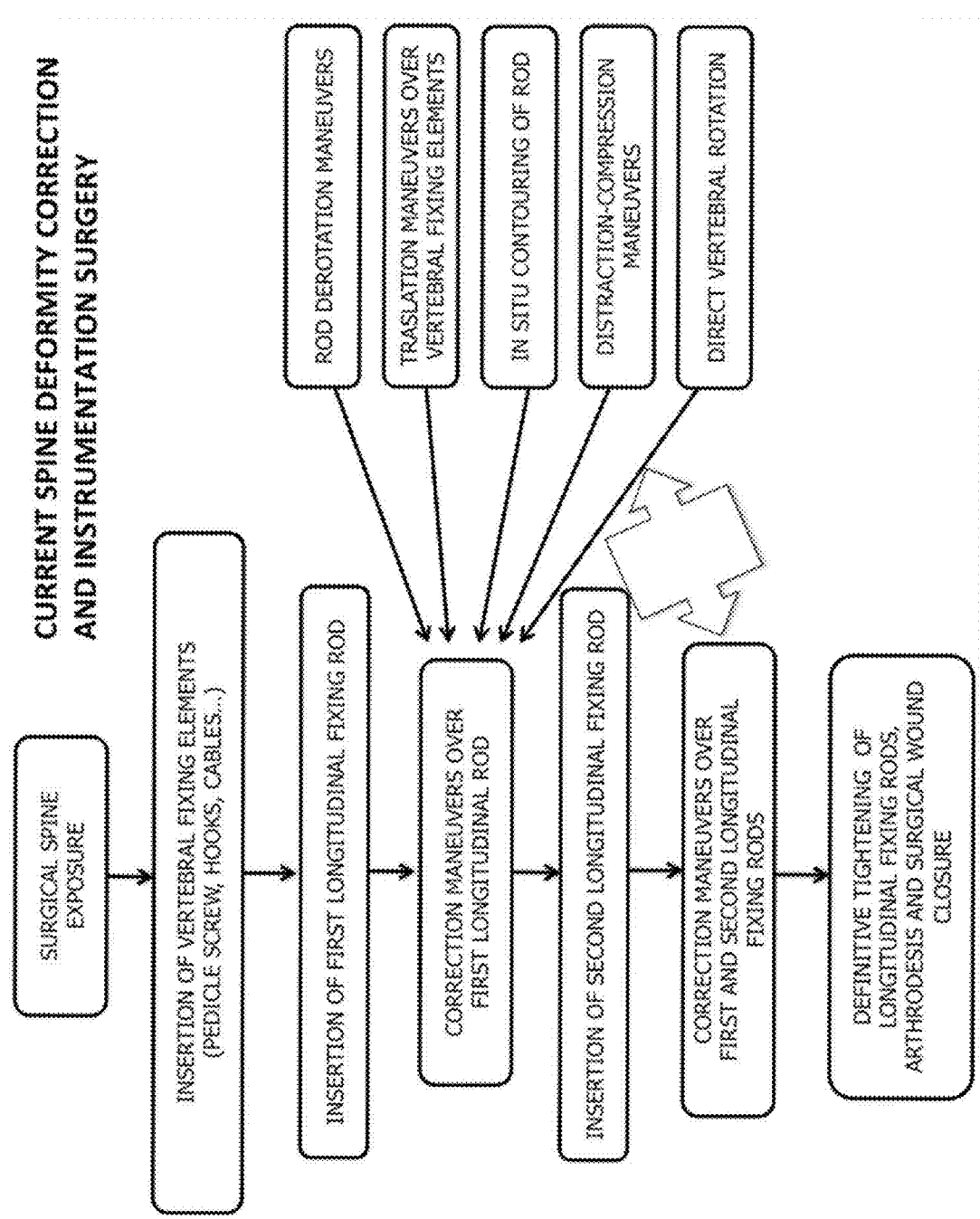
FIG. 25 illustrates a scheme of the process of current correction and fixation of spine deformities using conventional existing surgical instrumentations.

FIG. 24 illustrates the process of the present invention as compared to the current process of correction of a spine deformity using conventional surgical instrumentations as illustrated in FIG. 25.

The elements described in this disclosure used for the correction of spine deformities and vertebral displacements are different physically from the elements used for the definitive fixation of the spine and this characteristic constitutes a crucial element of this invention that distinguishes it from current and commonly used spine deformity correction instrumentations where the same longitudinal spinal fixing elements that are used for the correction of the spine are commonly utilized for the definitive fixation of the spine.

As disclosed herein the forces exerted by the correcting force element(s) over the polyaxial correcting elements are transformed, with the help of the sagittal positioning correction elements, the sagittal inclination correction elements and the frontal inclination correction elements, into an accurate and predictable mobilization of the polyaxial correcting elements and the vertebrae to where these polyaxial correcting elements are attached.

The constraints imposed to the forces exerted by the action of the correcting force elements upon the polyaxial correcting element are determined by the initial positioning of the polyaxial correcting element, by the adjustment and fixation of the sagittal positioning correction elements, the sagittal inclination correction elements, the frontal inclination correction elements and by the intrinsic anatomic resistance of each individual vertebrae within the spine to its mobilization.

As a unique characteristic of the method and apparatuses described in this invention, the final three-dimensional aspect of the spine being corrected can be determined before the surgical intervention by the careful evaluation of the deformity and the correct alignment and disposition of the correcting elements disclosed in this invention over the vertebrae being corrected.

As a direct consequence of the prior benefits and the elements described in this invention where the final three-dimensional aspect of the spine to be corrected can be determined and known before surgery, the definitive longitudinal spinal fixing elements can be custom pre-molded before surgery avoiding unnecessary intra-operative bending and contouring of these rods to the curvature of the corrected spine, therefore decreasing possible damage caused to the longitudinal spinal fixing elements during this intra-operative contouring that can decrease their strength and increase the chances for material failure.

As another consequence of knowing in advance the final three-dimensional aspect of a deformed spine that is to be surgically corrected with the help of the method and apparatuses described in this invention, the definitive longitudinal spinal fixing elements can be custom pre-molded before surgery in a way that they can be attached and fixed to the vertebral fixing elements or to the permanent vertebral connector elements in a pre-tensioned manner if desired so that no spine deformity correction is lost once all the temporary elements used for the correction of the spine as described in this invention are removed.

As another consequence of physically and temporarily separating the correction of the spine from the definitive fixation with longitudinal spinal fixing elements, both sides of the spine can be fixed at the same time and thus the longitudinal spinal fixing elements will equally share the same stresses and loads that the spine is subject to, diminishing the chances for material failure and for the loss of the spine deformity correction achieved.

As an exclusive feature of the methods and apparatuses disclosed in this invention the achieved final correction of the spine is not so dependent on the initial and precise positioning of the vertebral fixing elements that hold onto the vertebrae but rather on the design of the apparatuses depicted herein, the adequate placement of the correcting elements disclosed and the correction method of this invention that combined with an adequate evaluation and analysis of the spine deformity being treated will result in a satisfactory and expected final three-dimensional spine alignment.

The present invention further makes possible and includes a pre-surgical evaluation of the initial state of the spine and the creation of a careful plan of the desired spine deformity correction. This evaluation and planning process includes use of medical images of the spine, such as radiographs, computerized tomographic radiographs, nuclear magnetic resonance images and other medical images.

The preoperative surgical planning benefits from the aid of a computerized medical imaging system with three-dimensional reconstruction capabilities. It is envisioned that such imaging system is used in combination with a virtual image spine correction software package Such a package would allow the caregiver to visualize the initial three-dimensional state of the spine and also plan and pre-visualize the final and desired three-dimensional aspect of the spine once a determined correction is simulated.

The medical images software system and virtual image spine correction software package that aids the surgeon planning an adequate spine correction plan illustrates the initial state of the deformed spine as well as the image of the final corrected spine. This tool further provides the required spatial disposition of the polyaxial correcting elements, the sagittal positioning correction elements, the sagittal inclination correction elements and the frontal inclination correction elements to achieve the planned spine correction with the aid of the correcting force element(s).

It is contemplated that the medical images and virtual image spine correction software package is flexible enough to offer the surgeon the possibility to individually select a preferred positioning of the correcting elements described in this invention placed over the image of one or more of the vertebrae of the spine that the surgeon wants to correct and simulate the correction rendering an image of the spine correction achieved with these particular correcting elements disposition.

The flexibility and user friendliness of the medical images and virtual image spine correction software package will also permit the surgeon to determine a final desired aspect of the spine and the software will give in return the required position and alignment of the polyaxial correcting elements, the sagittal positioning correction elements, the sagittal inclination correction elements and the frontal inclination correction elements for each individual vertebrae of the spine in order to achieve the correction of the spine proposed by the user.

A wide variety of medical images and virtual image spine correction software packages for the adequate pre-surgical planning of the correction of the individual vertebrae and spine deformity as described in this invention can be designed and shall be considered an inherent and fundamental part of the invention when used for the correction of the spine in a similar manner as described in this invention.

In practice, where the surgical correction of a spine deformity is desired a caregiver will begin with preoperative planning of the correction to be done. Here, the caregiver provides a preoperative evaluation of the spine deformity with the aid of medical images in the form of scanners and other high definition images. The caregiver visualizes and analyzes the initial position in the three dimensional space of each vertebra to be corrected and the desired final position of this same vertebra after the desired correction to be done with the help of the methods and apparatuses disclosed in this invention.

This process of visualizing the initial state and the final state of the individual vertebrae and the whole spine is facilitated through the use of the medical image software integrated with the virtual spine correction software. The virtual spine correction software provides the necessary positioning for each of the correcting elements disclosed herein to allow the caregiver to move the deformed spine from its initial position to the final desired and corrected position. The virtual correction software can also propose different final corrections and give the adequate positioning of the correcting elements according to each of the corrections proposed. These possible corrections of the deformed spine can be stored in the computer system where the virtual spine correction software resides for a rapid intraoperative visualization of the different possible corrections of the deformed spine. Preferably the contemplated virtual spine correction software is also capable of rendering the aspect of the corrected spine for a determined positioning of the correcting elements provided herein as proposed by the caregiver evaluating the correction of the deformity.

Once a determined correction of the deformed spine has been considered surgical correction of the spine can proceed.

Surgery of the spine is done in a standard fashion and the subject is surgically prepared and the spine exposed.

Once the spine has been exposed, the surgeon inserts the vertebral fixing elements in the vertebral elements to be mobilized as planned.

When the vertebral fixing elements have been fixed to the vertebrae, the vertebral connectors are attached to the vertebral fixing elements of the same vertebra.

The polyaxial correcting elements are then connected to the vertebral connector elements with desired placement and angles related to the vertebrae as planned. Planning and placement concerns both correct angles to be used in axial plane, the sagittal plane and also the rotation as viewed in the coronal plane.

The sagittal positioning correction elements are placed along the polyaxial correcting elements in the desired pre-planned position for each vertebral element.

The sagittal inclination correction elements are placed in the desired and pre-planned position at each polyaxial correcting element.

The frontal inclination correction elements are placed in the desired and pre-planned position along each polyaxial correcting element.

With the intention of facilitating the work of the caregiver and diminish the surgical time, all the correcting elements to be placed on the polyaxial correcting elements can be prepared before the surgery begins or can be prepared while the spine is being exposed by an assistant following the precise instructions given by the caregiver for the adequate placement of the correcting elements in each individual polyaxial correcting element.

Once all the correcting elements are placed in situ and the polyaxial correcting elements fixed to the vertebral connector elements as desired and pre-planned, the correcting force element(s) can be placed along/over/through the polyaxial correcting elements, the sagittal positioning correction elements, the sagittal inclination correction elements and the frontal inclination correction elements, depending of the final design of the correcting force element(s), to exert the correcting force on the polyaxial correcting elements and the other correcting elements that are disclosed herein, and thus mobilize the vertebrae to its proper and final corrected position.

In one embodiment as described herein, the correcting force is provided by various flexible alloy cables that can be tensioned after being introduced along the polyaxial correcting elements, the sagittal positioning correction elements and the frontal inclination correction elements being the sagittal inclination correction elements placed along the polyaxial correcting elements. In this embodiment the spine can be corrected by the manual tensioning of the cables or the spine can be corrected by the action of a power driven correcting force element(s) such as a power driven cable over a previously specified period of time while the caregiver(s) can perform further surgical liberation of the osseous, capsular or ligamentous structures of the spine along the vertebrae being corrected if such action is considered necessary or appropriate in order to facilitate the mobilization of these vertebral elements. At the same time as the correction of the deformity of the spine by the slow action of a power driven correcting force, the caregiver(s) can prepare the athrodesis of the osseous elements in the form of exposing the undersurface of the posterior elements of the vertebrae if desired.

If the correction of the spine is considered satisfactory or sufficient by the caregiver(s) at any time during the process of spine deformity correction, the action of the correcting force element(s) can be detained/halted and a definitive fixation of the vertebral fixing elements can be accomplished with the longitudinal spinal fixing elements.

Once the correction of the spine has been completed, the caregiver(s) can introduce and fix the longitudinal spinal fixing elements in the vertebral fixing elements. Both sides of the vertebral column can be fixed with longitudinal spinal elements at the same time. In an ideal situation the longitudinal spinal fixing elements are custom pre-molded before surgery and the pre-molding of these spinal fixing elements is done so as that these are introduced and fixed to the vertebral fixing elements in a pre-tensioned form.

When a corrective force is applied the vertebral fixing elements and the other correcting elements are also put under a stress/strain force as the deformed spine is coaxed to its final correction state. If the longitudinal fixing rods used have same contour as the planned correction, when fixed to the vertebral fixing elements, or to the permanent vertebral connectors, the pre-contoured longitudinal fixing rod will bear reduced stresses/strains until the correcting force elements are removed. At this point in time, the pre-contoured longitudinal fixing rods will resist the deformation forces of the corrected spine and therefore will eventually somehow suffer a slight deformation under these forces, leading to some losing of the deformity correction achieved within time.

Preferably, the longitudinal fixing rods are not introduced exactly contoured to the deformity obtained intraoperatively, rather the longitudinal fixing rods are slightly "overcorrected" so that when they are attached and fixed to the vertebral fixing elements, or permanent vertebral connectors, they are already being subject to a force in the direction of the correction of the deformed spine. In this embodiment, the longitudinal fixing rods do not deform as much after removal of the correcting force elements, and therefore the spine deformity correction achieved intraoperatively is not lost as much over time. As used herein pre-stressed longitudinal fixing rods refer to these overcorrected longitudinal fixing rods.

Once the longitudinal spinal fixing elements have been introduced and securely fixed to the vertebral fixing elements, the correcting force element(s)s can be loosened and removed. After the removal of the correcting force element(s) has been done, the polyaxial correcting element(s) with the correcting element(s) attached thereto and the temporary vertebral connector elements can be removed.

After the vertebral connector elements have been removed, the protruding stem part of the vertebral fixing elements, employed for joining together solidly the vertebral fixing elements with the aid of the vertebral connector element(s) in the embodiment shown in this invention, can be cut and/or shortened to avoid protrusion under the skin of the patient.

Within this invention are contained all the necessary elements to intra-operatively visualize the correction being done by obtaining computer rendered images that reflect the three dimensional aspect of the spine as it is being corrected. In one possible embodiment, one, two or more infrared detectors or other type of spatial detectors are used to determine precisely the spatial positioning of the polyaxial correcting elements described herein. Similarly, such spatial detectors can provide spatial positioning of any other elements being used in the correction of the vertebrae, including but not limited to temporary or permanent vertebral connectors, vertebral correcting elements placed along the polyaxial correcting elements, and/or correcting force elements. In one embodiment, rendered images of the vertebrae of the misaligned spine obtained from the medical images studies are used as an initial reference so that the progressive mobilization of the polyaxial correcting element(s) and other correcting elements attached to the vertebrae are detected and registered by the spatial detectors. The corresponding spatial mobilization of the vertebrae are then determined by a computer or similar device and represented on one or more monitor or viewing screens. This representation of the spine being corrected provides the caregivers with additional information related to the correction above and beyond the visualization of the back of the spine that the caregivers have in the operating theater. This information that can be used by the caregivers to modify the correction planned or alter the correction being done.

In one embodiment a system of correction is contemplated as follows: a/ one or more cables are used to provide corrective force as described herein; b/ a system is in place for detecting the spatial positioning of the polyaxial correcting elements, the vertebral correcting elements and the vertebrae to which these are attached; c/ the intra-operatively force exerted during the correction maneuvers over the cables used as correcting force elements is measured; d/ the precise direction of the cables going through the polyaxial correcting elements and the vertebral correction elements is determined; and the data is used intra-operatively to continuously calculate and display the force exerted on the vertebral fixing elements and the vertebrae.

In an alternate embodiment. a coloring method can also be used to display the data obtained and an alert can be set so that the caregivers know when the force exerted on one or more vertebral fixing elements or vertebrae are near or over a certain threshold. In one embodiment such thresholds are predetermined by the computer or alternatively selected individually by the caregivers taking into consideration individual characteristics of the patient including sex, age and bone quality among others.

Knowledge of the forces exerted over the vertebral fixing elements or the vertebrae provides caregivers additional information on the need to detain or modify the correction, or the need to perform additional surgical procedures to facilitate the three-dimensional mobilization of the affected vertebra or vertebrae thus making the correction maneuver safer for the patient and the surgical instrumentation.

As disclosed herein correcting force(s) is/are distributed/shared throughout the vertebrae. The proper design of all the elements of this invention allows for an efficient use of these forces, such that the forces applied to each vertebra are slowly and continuously incremented as the correcting force is applied, and these forces are transformed into vertebral mobilization following an individualized non-deterministic "free path" towards a final and preplanned state. There is not an "imposition" on each individualized vertebra forcing a specific rotation or translation, but rather the energy applied to each vertebra is transformed into rotation or translation in the three dimensional space following a less-energy path for each subsequent increments of the correcting force. This is opposed to other non-balanced distribution use of the correcting forces employed in most common spine deformity correction systems where the vertebral fixing elements are successively approach to the longitudinal rod used for the correction of the spine, or the longitudinal rod is approached successively to each vertebral fixing element, such that the correcting maneuvers provide peaks of forces acting on the individualized vertebral fixing elements that are being used at any time.

Similarly, the combination of the designs of the polyaxial correcting elements, the other vertebral correcting elements and the correcting force elements, as described herein, provide for a continuous and smooth correction of the vertebrae and the spine, an approach employing in a more convenient and balanced way, the forces employed with the action of the correcting force elements. The present invention thereby diminishes the chances for the intraoperative failure of the supporting vertebrae being corrected and therefore diminish the chances for adverse intraoperative of postoperative complication derived from the failure of these vertebrae or the non-desired mobilization of the vertebral fixing elements.

A surgical kit for correcting deformity of a spine in a patient in need is also provided herein. Elements of such a kit have been described with particularity earlier in this document. These elements can include but are not limited to: vertebral fixing element(s), vertebral connector element(s), polyaxial correcting element(s), sagittal positioning correction element(s), sagittal inclination correction element(s), frontal inclination correction element(s), corrective force element(s), and longitudinal spinal fixing elements.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, since numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of correcting a deformity of a spine in a patient in need thereof, comprising:
   a pre-operative stage and an operative stage;
   wherein said pre-operative stage comprises the steps of:
   analyzing an initial position of one or more vertebrae of said deformed spine;
   determining a pre-planned final position of said one or more vertebrae; and
   determining placement positions of one or more vertebral correcting elements based on said pre-planned final position of said one or more vertebrae; and
   wherein said operative stage comprises the steps of:
   surgically exposing said spine;
   inserting and affixing at least one set of vertebral fixing elements to said one or more vertebrae;
   placing one or more vertebral connector elements, wherein said one or more vertebral connector elements join individual vertebral fixing elements of said set of vertebral fixing elements;
   placing said one or more vertebral correcting elements, wherein said one or more vertebral correcting elements comprise polyaxial correcting elements sagittal positioning correction elements, sagittal inclination correction elements, and frontal inclination correction elements;
   wherein said polyaxial correcting elements are attached and fixed to a distal end of said vertebral connector elements or to said vertebral fixing elements;
   wherein said sagittal positioning correction elements are attached to said polyaxial correcting elements at a pre-planned distance from a distal end of said polyaxial correcting elements;
   wherein said sagittal inclination correction elements are attached to said polyaxial correcting elements at a pre-planned distance from said distal end of said polyaxial correcting elements;
   wherein said frontal inclination correction elements are attached to said polyaxial correcting elements at a pre-planned distance from said distal end of said polyaxial correcting elements;
   placing and tightening one or more corrective force elements, wherein said one or more correcting force elements act upon at least one of said polyaxial correcting elements, said sagittal positioning correction elements, said sagittal inclination correction elements, or said frontal inclination correction elements;
   placing and tightening of one or more longitudinal spinal fixing elements to said vertebral fixing elements or one or more said vertebral connector elements;
   removing said one or more corrective force elements; and
   removing said one or more polyaxial correcting elements, sagittal positioning correction elements, sagittal inclination correction elements and frontal inclination correction elements.

2. The method of claim 1, wherein said distal end of said one or more vertebral connector elements is of a shape corresponding to said distal end of said one or more polyaxial correcting elements, wherein said distal end of said one or more vertebral connector elements is nestable within said distal end of said one or more polyaxial correcting elements; and wherein said distal end of said one or more vertebral connector elements is spherical, approximately spherical, or otherwise allows for polyaxial mobilization, orientation or fixation of said one or more polyaxial correcting elements in relation to said one or more vertebral connector elements and in relation to said vertebrae of said spine.

3. The method of claim 1, wherein correcting forces are provided by a method selected from the group consisting of a cable tensioning system, a lateral compression rod system, a lateral closing clamp system, a lateral compression system, an articulating rod system, a lateral closing articulating clamps system, and combinations thereof.

4. The method of claim 3, wherein said correcting forces are provided by said cable tensioning system, wherein said cable tensioning system comprises a plurality of cables acting on one or more of said one or more polyaxial correcting elements, said one or more sagittal positioning correction elements, said one or more sagittal inclination correction elements, or said one or more frontal inclination correction elements, wherein said cable tensioning system is manually driven or power driven.

5. The method of claim 4, wherein said correcting forces are measured and monitored in real-time, and wherein a visual or audible notification is provided if said correcting forces reach a pre-established threshold.

6. The method of claim 1, wherein said one or more longitudinal spinal fixing elements are custom pre-molded.

7. A surgical kit adapted to correct a deformity of a spine in a patient in need thereof, comprising: one or more vertebral fixing elements; optionally one or more vertebral connector elements, wherein said one or more vertebral connector elements provide a means for joining each of a pair of said one or more vertebral fixing elements when said pair of vertebral fixing elements are attached to one vertebrae; one or more polyaxial correcting elements attachable to said one or more vertebral connector elements or said vertebral fixing elements, said one or more polyaxial correcting element having a distal end for attachment and fixation to said one or more vertebral connector elements or to said one or more vertebral fixing elements; wherein said one or more polyaxial correcting elements are adapted to correct alignment of said vertebrae in a frontal plane and correct inclination of said vertebrae in the axial plane; one or more sagittal positioning correction elements, wherein said one or more sagittal positioning correction elements are adapted to correct alignment of said vertebrae in a sagittal plane and are attachable to said one or more polyaxial correcting elements; one or more sagittal inclination correction elements, wherein said one or more sagittal inclination correction elements are adapted to correct inclination of said vertebrae in a sagittal plane and are attachable to said one or more polyaxial correcting elements; one or more frontal inclination correction elements, wherein said one or more frontal inclination correction elements are adapted to correct inclination of said vertebrae in a frontal plane and are attachable to said one or more polyaxial correcting elements; one or more corrective force elements adapted to promote alignment of vertebrae by acting upon said one or more polyaxial correcting elements, said one or more sagittal positioning correction elements, said one or more sagittal inclination correction elements and said one or more frontal inclination correction elements; one or more pre-molded longitudinal spinal fixing elements attachable to said one or more vertebral connector elements or to said one or more vertebral fixing elements.

8. A method of correcting a spinal deformity comprising:
analyzing an initial position of one or more vertebrae of the deformed spine;
determining a pre-planned final position of the one or more vertebrae; and
determining placement positions of one or more vertebral correcting elements based on the pre-planned final position of the one or more vertebrae; and
surgically placing the one or more vertebral correcting elements in the determined placement positions; and
applying corrective forces to the one or more vertebral correcting elements such that the one or more vertebrae are mobilized into substantially the pre-planned final position,
pre-operatively determining sizing of the one or more vertebral correcting elements based on the pre-planned final position of the one or more vertebrae, wherein the vertebral correcting elements provide a pre-determined final sagittal alignment of the one or more vertebrae in a sagittal plane, a pre-determined final sagittal inclination of the one or more vertebrae in a sagittal plane, a pre-determined final frontal inclination of the one or more vertebrae in a frontal plane, a pre-determined final frontal alignment of the one or more vertebrae in a frontal place, and a pre-determined axial inclination of the one ore more vertebrae in an axial plane,
wherein the one or more vertebral correcting elements comprise polyaxial correcting elements and at least one of sagittal positioning correction elements, sagittal inclination correction elements, and frontal inclination correction elements, and
attaching a set of vertebral fixing elements to each of the one or more vertebrae of a spine;
placing the one or more vertebral connector elements to join individual vertebral fixing elements of the set of vertebral fixing elements attached to each particular vertebrae; and
attaching the polyaxial correcting elements to a distal end of the vertebral connector element or to a distal end of the vertebral fixing element and wherein the at least one of sagittal positioning correction elements, sagittal inclination correction elements, or frontal inclination correction elements are attached to and placed at a pre-planned distance from a distal end of the one or more polyaxial correcting elements.

9. The method of claim 8, further comprising:
forming custom pre-molded longitudinal fixing elements based on the pre-planned final position of the one or more vertebrae.

10. The method of claim 9, wherein the custom pre-molded longitudinal fixing elements are fixed to the one or more vertebral fixing elements or to the one or more vertebral connector elements in a pre-tensioned form.

11. The method of claim 8, wherein the corrective forces are applied by a cable tensioning system having a plurality of cables, wherein each of the cables act upon one or more of the vertebral correcting elements.

12. The method of claim 8, wherein the corrective forces are applied in a pre-determined manner.

13. The method of claim 8, further comprising:
monitoring the application of the corrective forces in real-time.

14. The method of claim 13, wherein the real-time monitoring provides alerts to the caregivers when the corrective forces applied meet the pre-established levels.

15. The method of claim 14, wherein the real-time monitoring provides alerts to the caregivers when the corrective forces applied exceed the pre-established levels.

16. The method of claim 13, wherein the real-time information is used to modify the pre-planned final position of the vertebrae.

\* \* \* \* \*